US006361885B1

(12) United States Patent
Chou

(10) Patent No.: US 6,361,885 B1
(45) Date of Patent: Mar. 26, 2002

(54) ORGANIC ELECTROLUMINESCENT MATERIALS AND DEVICE MADE FROM SUCH MATERIALS

(75) Inventor: Homer Z. Chou, Schaumburg, IL (US)

(73) Assignee: Organic Display Technology, Chicago, IL (US)

( * ) Notice: Subject to any disclaimer, the term of this patent is extended or adjusted under 35 U.S.C. 154(b) by 0 days.

(21) Appl. No.: 09/196,672

(22) Filed: Nov. 19, 1998

Related U.S. Application Data

(63) Continuation-in-part of application No. 09/172,843, filed on Oct. 15, 1998, and a continuation-in-part of application No. 09/173,393, filed on Oct. 15, 1998.
(60) Provisional application No. 60/081,277, filed on Apr. 10, 1998.

(51) Int. Cl.$^7$ .......................... H05B 33/14; C09K 11/06; C08G 77/00
(52) U.S. Cl. ....................... 428/690; 428/917; 428/447; 428/448; 313/504; 257/40; 257/103; 528/33; 528/40; 252/301.35
(58) Field of Search ................................. 428/690, 917, 428/447, 448, 450; 313/504, 506; 257/40, 103; 528/33, 40, 43; 252/301.35

(56) References Cited

U.S. PATENT DOCUMENTS

| | | | | |
|---|---|---|---|---|
| 4,595,599 A | * | 6/1986 | Brown et al. ................... | 427/5 |
| 4,822,716 A | * | 4/1989 | Onishi et al. ................ | 430/192 |
| 5,156,918 A | | 10/1992 | Marks et al. ................ | 428/447 |
| 5,281,489 A | * | 1/1994 | Mori et al. .................. | 428/690 |
| 5,409,783 A | | 4/1995 | Tang et al. .................. | 428/690 |
| 5,674,635 A | | 10/1997 | Hsieh et al. ................. | 428/690 |
| 5,834,100 A | * | 11/1998 | Marks et al. ................ | 428/209 |
| 6,059,553 A | * | 5/2000 | Jin et al. .................... | 421/387 |

FOREIGN PATENT DOCUMENTS

| | | |
|---|---|---|
| WO | WO 94/15368 | 7/1994 |
| WO | WO 97/49548 | 12/1997 |

OTHER PUBLICATIONS

Status of and prospectus for organic electroluminescence (Commentaries and Reviews, Journal of Materials Research vol. 11, No. 12) Lewis J. Rothberg and Andrew J. Lovinger, Bell Laboratories, Lucent Technologies, Murray Hill, New Jersey 07974, pp. 3174–3187, Dec. 1996.
Organic Light Emitters Gain Longevity, Science, vol. 273. Aug. 16, 1996, Robert F. Service, pp. 878–880.
Recombination Radiation in Anthracene Crystals, W. Helfrich and W. G. Schneider, Division of Pure Chemistry, National Research Council, Ottawa, Canada, vol. 14, No. 7 Feb. 15, 1965, Physical Review Letters, pp. 229–231.
Double Injection Electroluminescence in Anthracene, J. Dresner, RCA Laboratories, Princeton, N.J. , pp. 322–334, RCA Review, date not give.
Electrical Conduction and Low Voltage Blue Electroluminescence in Vacuum–Deposited Organic Films, P.S. Vincett, W. A. Barlow and R. A. Hann. G.G. Roberts, source, date and page numbers not given.
Organic electroluminescent diodes, C. W. Tang and S. A. Van Slyke, Research Laboratories, Corporate Research Group, Eastman Kodak Company, Rochester, New York 14650, pp. 913–915, Sep. 21, 1987, Appl. Phys. Lett. 51(12).
Molecular design of hole transport materials for obtaining high durability in organic electroluminescent diodes, Chihaya Adachi, Kazukiyo Nagai, and Nozomu Tamoto, Chemical Products R&D Center, Rico Co., Ltd. pp. 2679–2681, May 15, 1995, Appl. Phys. Lett. 66(20).
Electroluminescence from trap–limited current transport in vacuum deposited organic light emitting devices, P.E. Burrows and S. R. Forest, Advanced Technology Center for Photonics and Optoelectronic Materials, Princeton University, pp. 2285–2287, Apr. 25, 1994, Appl. Phys. Lett. 64(17).
Multilayered organic electroluminescent device using a novel starburst molecule, 4.4', 4"–tris (3–methylphenylamino) triphenylamine, as a hole transport material, Yasuhiko Sirota, Yoshiyuki Kuwabara, and Hiroshi Inada, Department of Applied Chemistry, Faculty of Engineering, Osaka University, Takeo Wakimoto, Hitoshi Nakada, Yoshinobu Yonemoto, Shin Kawami, and Kunio Imai, Corporate R&D Laboratory, Pioneer Electronic Corporation, pp. 807–809, Aug. 15, 1994, Appl. Phys. Lett. 65(7).
Metal ion dependent luminescence effect in metal tris–quinolate organic heterojunction light emitting devices, P.E. Burrows, L.S. Sapochak, D.M. McCarty, S.R. Forrest and M. E. Thomspon, Advanced Technology Center for Photonic and Optoelectornic Materials, Princeton University, pp. 2718–2720, May 16, 1994, Appl. Phys. Lett. 64(20).
A Novel Blue Light Emitting Material Prepared from 2–(o–Hydroxyphenyl)benzoxazole, Norikazu Nakamura, Shinichi Wakabayashi, Keiichi Miyairi and Tsunceo Fujii, Shinko Electric Industries Co., Ltd., Department of Electrical and Electronic Engineering, Faculty of Engineering, Shinshu University, Department of Chemistry and Materials Engineering, Faculty of Engineering, Shinshu University, Chemistry Letters pp. 1741–1742, 1994, (no month).

(List continued on next page.)

Primary Examiner—Marie Yamnitzky
(74) Attorney, Agent, or Firm—Wallenstein & Wagner, Ltd.

(57) ABSTRACT

Electroluminescent devices and materials including an electroluminescent organo-siloxane polymer. The main chain of the organo-siloxane polymer comprises an organic component that can be alkenyl, alkynyl, aralkyl, aryl, heteroaralkyl, and heteroaryl which can be substituted optionally with hydrogen, alkyl, aryl, heteroalkyl, heteroaralkyl, nitro, cyano, hydroxy, alkoxy, aryloxy, thio, alkylthio, arylthio, amino, halogen, dialkylamino, diarylamino, diaralkylamino, arylamino, alkylamino, arylalkylamino, carbonyloxy, carbonylalkoxy, carbonylalkyloxy, alkylcarbonyloxy, arylcarbonyloxy, alkoxylcarbonyloxy, sulfonyl, or sulfonyloxy. The organic component includes at least two covalent bonds coupling the organic component to the main chain of the organo-siloxane polymer. Such devices provide superior performance and mechanical stability compared with conventional organic electroluminescent materials and devices made from such materials.

49 Claims, 4 Drawing Sheets

OTHER PUBLICATIONS 1,2,4–Triazol Derivative as an Electronic Transport Layer in Organic Electroluminescent Devices, Junji Kido, Chikay Ohtaki, Kenichi Hongawa, Katsuro Okuyama and Katsutoshi Nagai, Department of Materials Science and Engineering, Yamagata University, Department of Electrical and Information Engineering, Yamagato University, pp. 917–920, Jpn. J. Appl. Phys., Jul. 1993.

Blue–Light–Emitting Organic Electroluminescent Devices with Oxadiazole Dimer Dyes as an Emitter, Yuji Hamada, Chihaya Adachi, Tetsuo Tsutsui and Shogo Saito, Department of Materials Science and Technology, Graduate School of Engineering Sciences, Kyushu University, pp. 1812–1816, Jpn. J. Appl. Phys., 1992 (no month).

Highly efficient blue electroluminescence from a distyrylarylene emitting layer with a new dopant. Chishio Hosokawa, Hisahiro Higashi, Hioraki Nakamura, and Tadashi Kusumoto, Central Research Laboratories, Idemitsu Kosan Co., Ltd., pp. 3853–3855, Dec. 25, 1995, Appl. Phys. Lett. 67(26).

Organic Electroluminescent Device with a Three–Layer Structure, Chihaya Adachi, Shizuo Tokito, Tetsuo Tsutsui and Shogo Saito, Department of Materials Science and Technology, Graduate School of Engineering Sciences, Kyushu University, pp. 713–715, Apr. 1998, source not given.

Bright red light–emitting organic electroluminescent devices having a europioum complex as an emitter, Junji Kido, Hiromichi Hayase, Kenichi Hongawa, Katsutoshi Nagai, and Katsuro Okuyama, Department of Materials Science and Engineering, Yamagata University, pp. 2124–2125, Oct. 24, 1994, Appl. Phys. Lett. 65(17).

Electroluminescent Diodes from a Single–Component Emitting Layer of Dendritic Macromolecules, Pei–Wei Wang, Yu–Ju Liu, Chelladurai Devadoss, P. Bharathi and Jeffrey S. Moore, Adv. Mater, 1996, 8, No. 3, pp. 237–241. (no month).

Blue light–emitting organic electroluminescent devices, Chihaya Adachi, Tetsuo Tsutsui, and Shogo Saito, Department of Materials Science and Technology, Graduate School of Engineering Sciences, Kyushu University, pp. 799–801, Feb. 26, 1990, Appl. Phys. Lett. 56(9).

Electroluminescence in Organic Films with Three–Layer Structure, Chihaya Adachi, Shizuo Tokito, Tetsui Tsutsui and Shogo Saito, Department of Materials Science and Technology, Graduate School of Engineering Sciences, Kyushu University, pp. L269–L271, source and date not given.

Organic electroluminescent devices fabricated using a diamine doped $MgF_2$ thin film as a hole–transporting layer, Shizuo Tokito and Yasunori Taga, Toytoa Central Research & Development Laboratories, Inc., Appl. Phys. Lett/ 66(6), Feb. 6, 1995 pp. 673–675.

Organic electroluminescent device having a hole conductor as an emitting layer, Chihaya Adachi, Tetsuo Tsutsui and Shogo Saito, Department of Materials Science and Technology, Graduate School of Engineering Sciences, Kyusha University, Appl. Phys. Lett. 55(15), Oct. 9, 1989, pp. 1489–1491.

Electroluminescence of doped organic thin films, C. W. Tang, S.A. Van Slyke and C. H. Chen, Corporate Research Laboratories, Eastman Kodak Company, J. Appl. Phys. 65(9), May 1, 1989, pp. 3610–3616.

Multilayer White Light–Emitting Organic Electroluminescent Device, Junji Kido, Masato Kimura, Katsutoshi Nagai, Science, Vo. 267, Mar 3, 1995, pp. 1332–1334.

Organic Multilayer White Light Emitting Diodes, Marki Strukelj, Rebecca H. Jordan and Ananth Dodabalapur, J. Am. Chem. Soc. 1996, 118, pp. 1213–1214. (no month).

White organic electroluminescence devices, R. H. Jordan, A. Dodabalapur, M. Strukelj, T. M. Miller, Appl. Phys. Lett. 68 (9), Feb. 26, 1996, pp. 1192–1194.

Reliability and degradation of organic light emitting devices, P. E. Burrows, V. Bulovic, S. R. Forrest, L. S. Sapochak, D. M. McCarty and M. E. Thompson, Advanced Technology Center for Photonic and Optoelectronic Materials, Princeton University, Appl. Phys. Lett. 65(23), Dec. 5, 1994, pp. 2922–2924.

Observation of degradation processes of Al electrodes in organic electroluminescence devices by electroluminescence microscopy, atomic force microscopy, scanning electron microscopy, and Auger electron spectroscopy, L. M. Do, e. M. Han, Y. Niidome and M. Fujihira, Department of Biomolecular Engineering, Tokyo Institute of Technology, T. Kanno, S. Yoshida, A. Maeda and A. J. Ikushima, Materials Research Laboratory, HOYA Corporation, J. Appl. Phys. 76(9), Nov. 1, 1994, pp. 5118–5121.

Study of Interfacial Degradation of the Vapor–Deposited Bilayer of Alq3/TPD for Organic Electroluminescent (EL) Devices by Photoluminescence, Eun–Mi Han, Lee–Mi Do, Noritaka Yamamoto and Masamichi Fujihira, Department of Biomolecular Engineering, Tokyo Institute of Technology, Chemistry Letters 1995, pp. 57–58. (no month).

Effects of Plasma Modification on Hole Transport Layer in Organic Electroluminescent Diode, Tatsuo Mori, Seiya Miyake and Teryoshi Mizutani, School of Engineering, Nagoya University, pp. 845–848, Jpn. J. Appl. Phys., 1995. (no month).

Anodic Oxidation Pathways of Aromatic Amines. Electrochemical and Electron Paramagnetic Resonance Studies, Eddie T. Seo, Robert F. Nelson, John M. Fritsch, Lynn S. Marcoux, Donald W. Leedy, Ralph N. Adams, Department of Chemistry, University of Kansas, Journal of the American Chemical Society [88:15] Aug. 5, 1966, pp. 3498–3503.

Observation of Crystallization of Vapor–deposited TPD Films by AFM and FFM, Eun–mi Han, Lee–mi–Do, Yasuro Niidome and Masamichi Fujihira, Department of Biomolecular Engineering, Tokyo Institute of Technology, Chemistry Letters, ©1994 The Chemical Society of Japan, pp. 969–970. (no month).

White–Light–Emitting Material for Organic Electroluminescent Devices, Yuji Hamada, Takeshi Sano, Hiroyuki Fuji, Yoshitaka Nishio, Hisakaza Takahashi and Kenichi Shibata, New Materials Research Center, Sanyo Electric Co. Jpn. J. Appl. Phys. vol. 35, Part 2, No. 10B, Oct. 15, 1996, pp. 1339–1341.

Metal oxides as a hole–injecting layer for an organic electroluminescent device, Shizuo Tokito, Koji Noda and Yasunori Taga, Toyota Central Research and Development Laboratories, Inc., pp. 2750–2753, © 1996, source not given. (no month).

Durability Characteristics of Aminopyrene Dimer Molecules as an Emitter in Organic Multilayered Electroluminescent Diodes, Chihaya Adachi, Kazukiyo Nagai and Nozomu Tamoto, Chemical Products R&D center, Ricoh Co., Ltd., Jpn. J. Appl. Phys. vol. 35 Part 1, No. 9A, Sep. 1996, pp. 4819–4825.

Enhanced electron injection in organic electroluminescence devices using an Al/LiF electrode, L. S. Hung, C. W. Tang, M. G. Mason, Imaging Research and Advanced Development, Eastman Kodak Company, Appl. Phys. Lett. 70(2), Jan. 13, 1997, pp. 152–154.

Fabrication of electron injecting Mg:Ag alloy electrodes for organic light–emitting diodes with radio frequency magnetron sputter deposition, Hiroyuki Suzuki, NTT Basic Research Laboratories, Appl. Phys. Lett. 69(11), Sep. 9, 1996, pp. 1611–1613.

Growth of dark spots by interdiffusion across organic layers in organic electroluminescent devices, Masamichi Fujihira, Lee–Mi Do, Amane Koike and Eun–Mi Han, Department of Biomolecular Engineering, Tokyo Institute of Technology, Appl Phys. Lett. 68(12), Mar. 25, 1996, pp. 1787–1789.

Height of the energy barrier existing between cathodes and hydroxyquinoline–aluminum complex of organic electroluminescence devices, Michio Matsumura, Tomonori Akai, Masayuki Saito, and Takashi Kimura, Research Center for Photoenergetics of Organic Materials, Osaka University, J. Appl. Phys. 79(1) Jan. 1, 1996, pp. 264–268.

Novel hole–transporting materials based on triphenylamine for organic electroluminescent devices, Hiromitsu Tanaka, Shizuo Tokito, Yasunori Taga and Akane Okada, Toyota Central R & D Labs, Inc., Chem. Commun., 1996, pp. 2175–2176. (no month).

Organic Electroluminescent Devices Having Derivatives of Aluminum–Hydroxyquinoline Complex as Light Emitting Materials, Michio Matsumura and Tomonori Akai, Research Center for Photoenergetics of Organic Materials, Osaka University, Jpn. J. Appl. Phys. vol. 35, Part 1, No. 10, Oct. 1996, pp. 5357–5360.

A novel yellow–emitting material, 5,5"–bis{4–[bis(4–methylphenyl) amino]phenyl}–2,2':5',2"–terthiophene, for organic electroluminescent devices, Tetsuya Noda, Hiromitsu Ogawa, Naoki Noma and Yasuhiko Shirota, Appl. Phys. Letter 70(6), Feb. 10, 1997, pp. 699–701.

Surface modification of indium tin oxide by plasma treatment: An effective method to improve the efficiency, brightness, and reliability of organic light emitting devices, C.C. Wu, C. I. Wu, J. C. Sturm and A. Kahn, Department of Electrical Engineering, Advanced Technology Center for Photonic and Optoelectronic Materials, Princeton University, Appl. Phys. Lett. 70(11), Mar. 17, 1997, ©1997 American Institute of Physics, pp. 1348–1350.

Bright high efficiency blue organic light–emitting diodes with $Al_2O_3$/Al cathodes, H. Tang, F. Li and J. Shinar, Ames Laboratory–USDOE and Department of Physics and Astronomy, Iowa State University, Appl. Phys. Lett. 71(18), Nov. 3, 1997, pp. 2560–2562.

Highly efficient and bright organic electroluminsecent devices with an aluminum cathode, G. E. Jabbour, Y. Kawabe, S. E. Shaheen, J. F. Wang, M. M. Morrell, B. Kippelen and N. Peyghambarian, Optical Sciences Center, Univeristy of Arizona, Appl. Phys. Lett. 71(13), Sep. 29, 1997, pp. 1762–1764.

Lithium–aluminum contacts for organic light–emitting devices, E. I. Haskal, A. Curioni, P. F. Seidler and W. Andreoni, IBM Research Division, Zurich Research Laboratory, Appl. Phys. Lett. 71(9), Sep. 1, 1997, pp. 1151–1153.

Organic electroluminscence cells based on this films deposited by ultraviolet laser ablation, N. Matsumoto, H. Shima, T. Fujii and F. Kannan, Appl. Phys. Lett. 71(17), Oct. 27, 1997, pp. 2469–2471.

Low pressure organic vapor phase deposition of small molecular weight organic light emitting device structures, M. A. Baldo, V. G. Kozlov, P. E. Burrows and S. R. Forrest, Department of Electrical Engineering, Center of Photonics and Optoelectonic Materials, V. S. Ban, PS–LD Incorporated, B. Koene and M. E. Thompson, Department of Chemistry, University of Southern California, Appl. Phys. Lett. 71(21), Nov. 24, 1997, pp. 3033–3035.

Efficiency enhancement of microcavity organic light emitting diodes, R. H. Jordan, L. J. Rothberg, A. Dodabalapur and R. E. Slusher, Bell Laboratories, Lucent Technologies, Appl. Phys. Lett. 69(14), Sep. 39, 1996, pp. 1997–1999.

Strongly directed single mode emission from organic electroluminescent diode with a microcavity, Shizuo Tokito, Koji Noda and Yasunori Taga, Toyota Central Research and Development Labs, Inc., Appl. Phys. Lett. 68(19), May 6, 1996, pp. 2633–2635.

Photolithographic patterning of vacuum–deposited organic light emitting devices, P. F. Tian, P. E. Burrows and S. R. Forrest, Department of Electrical Engineering, Center for Photonics and Optoelectronic Materials, Appl. Phys. Lett. 71(22), Dec. 1, 1997, pp. 3197–3199.

Micropatterning Method for the Cathode of the Organic Electroluminescent Device, Kenichi Nagayama, Takashi, Yahagi, Hitoshi Nakada, Teruo Tohma, Teruichi Watanabe Kenji Yoshida and Satoshi Miyaguchi, Tohoku Pioneer Electronic Corporation, Corporate R & D. Laboratories, Pioneer Electronic Corporation, Jpn. J. Appl. Phys. vol. 36 (1997), Part 2, No. 11B, Nov. 15, 1997, pp. 1555–1557.

Organic solid–state lasers with imprinted gratings on plastic substrates, M. Berggren, A. Dodabalapur, R. E. Slusher, A. Timko and O. Nalamasu, Bell Laboratories, Lucent Technologies, Appl. Phys. Lett. 72(4), Jan. 26, 1998, pp. 410–411.

Temperature independent performance of organic semiconductor lasers, V. G. Kozlov, V. Bulovic and S. R. Forrest, Department of Electrical Engineering and the Princeton Materials Institute, Center for Photonics and Optoelectronic Materials, Appl. Phys. Lett. 71(18), Nov. 3, 1997, pp. 2575–2577.

Optically pumped blue organic semiconductor lasers, V. G. Kozlov, G. Parthasarathy, P. E. Burrows and S. R. Forrest, Department of Electrical Engineering and the Princeton Material Institute, Center for Photonocs and Optoelectronic Materials, Princteon University, Y. You and M. E. Thompson, Department of Chemistry, University of Southern California, Appl. Phys. Lett. 72(2), Jan. 12, 1998, pp. 144–146.

Stimulated emission and lasing in dye–doped organic thin films with Forster transfer, M. Berggren, A. Dodabalapur and R. E. Slusher, Bell Laboratories, Lucent Technologies, Appl. Phys. Lett. 71(16), Oct. 20, 1997, pp. 2230–2232.

Electroluminescence and electron transport in a perylene dye, P. Ranke, I. Bieyl, J. Simmerer and D. Haarer, A. Bacher and H. W. Schmidt, Universitat Bayreuth, Appl. Phys. Lett. 71(10), Sep 8, 1997, pp. 1332–1334.

Organic light–emitting diodes using 3– or 5–hydroxyflavone–metal complexes, Yuji Hamada, Takeshi Sano, Hiroyuki Fujii, Yoshitaka Nishio, Hisakaza Takahashi and Kenichi Shibata, New Materials Research Center, Sanyo Electric Company, Appl. Phys. Lett. 71(23), Dec. 8, 1997, pp. 3338–3340.

A Novel Family of Amorphous Molecular Materials Containing a Oligothiophene Moiety as Color–Tunable Emitting Materials for Organic Electroluminescent Devices, Tetsuya Noda, Hiromitsu Ogawa, Naoki Noma and Yasuhiko Shirota, Adv. Mater. 1997, 9, No. 9, pp. 720–721. (no month).

Deposition–induced photoluminescence quenching of tris–(8–hydroxyquinoline) aluminum, V. E. Choong, Y. Park and N. Shivaparan, Department of Physics and Astronomy, University of Rochester, C. W. Tang, Imaging Research and Advanced Development, Eastman Kodak, Co., Yo. Gao, Department of Physics and Astronomy, University of Rochester, Appl. Phys. Lett. 71(8), Aug. 25, 1997, pp. 1005–1007.

Low Molecular Weight and Polymeric Triphenylenes as Hole Transport Materials in Organic Two–Layer LEDs, Andreas Bacher, Ingo Bleyl, Christian H. Erdelen, Dietrich Haarer, Wolfgang Paulus and Hans–Werner Schmidt, Adv. Mater. 1997, 9, No. 13, pp. 1031–1035. (no month).

Control of Organic Interfaces with a Thin Film of Silicon Monoxide between 8–Hydroxyquinoline Aluminum and Diamine Layers in an Organic EL Diode, Yutaka Ohmori, Yoshitaka Kurosaka, Norio Tada, Akihiko Fujii and Katsumi Yoshino, Faculty of Engineering, Osaka University, Jpn. J. Appl. Phys., vol. 36, Part 2, No. 8A, Aug. 1, 1997, pp. 1022–1024.

Unoccupied molecular orbital states of tris (8–hydroxy quinoline) aluminum: Observation and dynamics, M. Probst and R. Haight, IBM T. J. Watson Research Center, Appl. Phys. Lett. 71(2), Jul. 14, 1997, pp. 202–204.

Electronic structure calculations of doped organic materials for electroluminescent devices, Shahul H. Nilar and M. W. C. Dharma–wardana, Institute for Microstructural Sciences, National Research Council, J. Appl. Phys. 82(2), Jul. 15, 1997, pp. 514–521.

The overshoot effect in transient electroluminescence from organic bilayer light emitting diodes: Experiment and theory, V. R. Nikitenko, V. I. Arkhipov, Y. H. Tak, J. Pommerehne and H. Bassler, H. H. Hörhold, J. Appl. Phys. 81(11), Jun. 1, 1997; pp. 7514–7525.

Charge carrier recombination in organic . . . , Y. H. Tak and H. Bassler, J. Appl., Phys. 81(10), May 15, 1997, pp. 6963–6967.

Interference phenomenon determines the color in an organic light emitting diode, Thomas Granlund and Leif a. A. Pettersson, Department of Physics and Measurement Technology, Laboratory of Applied Physics, Linköping University, Mats R. Anderson, Department of Organic Chemistry and Polymer Technology, Chalmers University of Technology, Olle Inganäs, Department of Physics and Measurement Technology, Laboratory of Applied Physics, Linköping University, J. Appl. Phys. 81(12), Jun. 15, 1997, pp. 8097–8103.

Organic electroluminescent devices with improved stability, S. A. Van Slyke, C. H. Chen and C. W. Tang, Imaging Resesearch and Advanced Development, Eastman Kodak Company, Appl. Phys. Lett. 69(15), Oct. 7, 1996, pp. 2160–2162.

Fluorescence Lifetime of Organic Thin Films Alternately Deposited with Diamine Derivative and Aluminum Quinoline, Tatsuo Mori, Kouji Obata, Kiyokazu Miyachi, Teruyoshi Mizutani and Yasuyuki Kawakami, Nagoya University, Jpn. J. Appl. Phys. vol. 36, Pt. 1, No. 12A, Dec. 1997, pp. 7239–7244.

Transient electroluminscence: Mobility and response time in quinquethiophene Langmuir–Blodgett films, A. J. Pal, Abo Akademi University, R. Österbacka, K. M. Källman and H. Stubb, Abo Akademi University, Appl. Phys. Lett. 71(2), Jul. 14, 1997, pp. 228–230.

Hydrogen–induced light emission from an organic electroluminescent device, Sumio Okuyama, Yasuaki Ito, Toshiyuki Sugawara, Katsuro Okuyama and Koichi Mastsushita, Yamagata University, Junji Kido, Yamagata University, Appl. Phys. Lett. 71(20), Nov. 17, 1997, pp. 2877–2879.

Accelerated hole transfer by double–layered metallophthalocyanine thin film for effective electroluminescence, Tsuyoshi Tominaga and Kohei Hayashi, The University of Tokyo, Naoki Toshima, University of Tokyo, Appl. Phys. Lett. 70(6), Feb. 10, 1997, pp. 762–763.

Electroluminescence of epitaxial perylene films, Toda and Yanagi, Kobe University, Appl. Phys., Lett. 69(16), Oct. 14, 1996, pp. 2315–2317.

Strongly directed single mode emission from organic electroluminescent diode with a microcavity, Tokito, Noda and Taga, Toyota Central Research and Development Labs, Inc., Appl. Phys. Lett. 68(19), May 6, 1996, pp. 2633–2635.

PPV Info Packet and references, source and date not given, 8 pages.

Light–emitting diodes based on conjugated polymers, Burroughs, Bradley, Brown, Marks, Mackay, Friend, Burns and Holmes, Letters to Nature, pp. 39–41. (date not given).

Charge Injection and Transport in Poly($_p$–Phenylene Vinylene) Light Emitting Diodes, Marks and Bradley, Cavendish Laboratory, Jackson, Burn and Holmes, University Chemical Laboratory, Synthetic Metals, 55–57 (1993), pp. 4128–4133.

Light–emitting diodes from partially conjugated poly(p–phenylene vinylene), Zhang, Braun and Heeger, J. Appl. Phys. 73(10), May 15, 1993, pp. 5177–5180.

Luminescence Enhancement by the Introduction of Disorder into Poly(p–phenylene vinylene), Son, Dodabalapur, Lovinger and Galvin, Science, vol. 269, Jul. 21, 1995, pp. 376–378.

Improved Efficiency in Semiconducting Polymer Light–Emitting Diodes, , D. Braun and A. J. Heeger, University of California, H. Kroemer, University of California, pp. 945–948, 1991, source not given. (no month).

Electroluminescence from light–emitting diodes fabricated from conducting polymers, D. Braun and A. J. Heeger, University of California, Thin Solid Films, 216 (1992) pp. 96–98. (no month).

Carrier tunneling and device characteristics in polymer light–emitting diodes, I. D. Par, UNAX Corporation, J. Appl. Phys. 75(3), Feb. 1, 1994, pp. 1656–1666.

Improved Efficiency in Polymer Light–Emitting Diodes Using Air–Stable Electrodes, Aratani, Zhang, Pakbax, Hoger, Wudl and Heeger, Institute for Polymers and Organic Solids, University of California, Journal of Electronic Materials, vol. 22, 1993, pp. 745–749. (no month).

Chlorine Precursor Route (CPR) Chemistry to Poly(p–phenylene vinylene)–Based Light Emitting Diodes, Hsieh, Antoniadis, Bland, Feld, Adv. Mater. 1995, 7, No. 1, pp. 36–38. (no month).

A Chlorine Precursor Route (CPR) to Poly(p–phenylene vinylene) Light Emitting Diodes, Hsieh and Antoniadis, University of Rochester, Bland and Feld, Wright State University, pp. 465–466, source and date not given.

Electroluminescence from Poly(p–phenylenevinylene)with monoalkoxy substitutent on the aromatic ring, Zyung, Kim and Hwang, Electronics and Telecommunications Research Institute, Hwang and Shim, Korean Advanced Institute of Science and Technology, Synthetic Metals 71 (1995) 2167–2169. (no month).

Novel Blue Electroluminescent Polymers with Well–Defined Conjugation Length, Taehyoung Zyung, Do–Hoon Hwang, In–Nam Kang, Hong–Ku Shim, Wol–Yon Hwang and Jang–Joo Kim, Electronics and Telecommunications Research Insitute, Chem. Mater. 1995, 7, pp. 1499–1503. (no month).

Polarized electroluminescence for rubbing–aligned poly(2, 5–dinonyloxy–1,4–phenylenevinylene) films, Hamaguchi and Yoshino, Osaka University, Appl. Phys. Lett. 67(23), Dec. 4, 1995, pp. 3381–3383.

Polymer Electroluminescence Using ac or Reverse cd Biasing, Yang, Hu and Karasz, University of Massachusetts, Macromolecules 1995, vol. 28, No. 18, pp. 6152–6154. (no month).

A Blue Light Emitting Polymer with Phenylenevinylene Segments in the Side–Chains, Hesemann, Vestweber, Pommerehne, Mahrt and Greiner, Adv. Mater. 1995, vol. 7, No. 4, pp. 388–389. (no month).

Efficient light–emitting diodes based on polymers with high electron effinities, Greenham, Moratti, Bradley, Friend and Holmes, University of Cambridge, Letters to Nature, 3 pages, date not given.

Conjugated Polymer Heterostructure Light–Emitting Diodes, Baigent, Cacialli. Friend, Greenham, Grüner, Holmes and Moratti, University Chemical Laboratory, pp. 452–453, source and date not given.

High Electron Affinity Polymers of LEDs, Moratti, Cervini, Holmes, Baigent, Friend, Greenbaum, Grüner and Hamer, University of Cambridge, Synthetic Metals 71, 1995, pp. 2117–2120, (no month).

Surface–emitting polymer light–emitting diodes, Baigent, Marks, Greenham, Friend, Moratti, Holmes, University Chemical Laboratory, Synthetic Metals 71 (1995) p. 2177. (no month).

Polymer electroluminescence in the near infra–red, Baigent, Hamer, Fried, Moratti, Holmes, University Chemical Laboratory, Synthetic Metals 71 (1995) p. 2175. (no month).

Red–Orange Electroluminescence with New Soluble and Air–Stable Poly(naphthalene–vinylenes)s, Tasch, Graupner, Leising, Pu, Wagner, Grubbs, Adv. Mater. 7, No. 11, pp. 903–906, 1995. (no month).

Visible–light electroluminescent diodes using poly(arylene vinylene), M. Onoda, Himeji Institute of Technology, Y. Ohmon, T. Kawai and K. Yoshino, Osaka University, Synthetic Metals 71 (1995) p. 2181. (no month).

Tunable Electroluminescence and Photoluminescence in Phenylenevinylene–Naphthylene–vinylene Copolymers, Faraggi, Chayet, Cohen, Neumann, Avny and Davidov, Adv. Mater. 1995, 7, No. 8, pp. 742–745. (no month).

Blue electroluminescence from a novel polymer structure, Baigent, Friend, Lee and Schrock, M.I.T., Synthetic Metals 71 (1995), p. 2171. (no month).

Stable Poly(Para–Phenylenes)s and their Application in Organic Light Emitting Devices, Grem, Martin, Meghdadi, Paar, Stampfl, Sturm, Tasch and Leising, Synthetic Metals 71 (1995) pp. 2183–2194. (no month).

Soluble Segmented Stepladder Poly(p–Phenylenes) for Blue–Light–Emitting Diodes, Grem, Paar, Stampfl, Leising Institut für Festkörperphysik, Huber and Scherf, Max-–Planck–Institut für Polymerforschung, Chem. Mater. 7, 1995 pp. 2–4. (no month).

On the Conjugation Length in Poly(para–phenylene)–Type Polymers, Grimme, Kreyenschmidt, Uckert, Müllen and Scherf, Adv. Mater. 1995, 7, No. 3, pp. 292–294. (no month).

Quantum Efficiencies of Electroluminescent Poly(Para–Phenylenes), Stampfl, Tasch, Leising and Schert, Synthetic Metals, 71 (1995), pp. 2125–2128. (no month).

Synthesis of Regioregular Poly(Methyl Pyridinium Vinylene): An Isoelectronic Analogue to Poly(Phenylene Vinylene), Marsella, Fu and Swager, Adv. Mater. 1995, 7, No. 2, pp. 145–147. (no month).

Photophysics of Poly(p–pyridine): Blue Electroluminescent Devices from a Soluble Conjugated Polymer, Jessen, Gebler, Wang and Blatchford, The Ohio State University, Lin and Gustafson, The Ohio State University, Wang, Swager and MacDiarmid, University of Pennsylvania, Eptein, The Ohio State University, pp. 573–574, source and date not given.

Photophysical Properties, Self–Assembled Thin Films, and Light–Emitting Diodes of Poly(p–pyridylvinylene)sand Poly(p–pyridinium vinylene)s, Tian, Wu, Thompson, Sturm and Register, Princeton University, Chem. Mater. 1995, vol. 7, No. 11, pp. 2190–2198. (no month).

Light–emitting diodes using n–type conducting polymer: Poly(p–pyridyl vinylene), Mitsuyoshi Onoda, Himeii Institute of Technology, J. Appl. Phys. 78(2), Jul. 15, 1995, pp. 1327–1333.

Symmetric light emitting devices from poly(p–di ethynylene phenylene) (p–di phenylene vinylene) derivatives, S. A. Jeglinski, University of Utah, O. Amir, Iowa State University, X. Wei and Z. V. Vardeny, University of Utah, J. Shinar and T. Cerkvenik Iowa State University, W. Chen and T. J. Barton, Iowa State University, Appl. Phys. Lett. 67(26), Dec. 25, 1995, pp. 3960–3962.

Flexible light–emitting diodes made from soluble conducting polymers, Gustafsson, Cao, Treacy, Klavetter, Colaneri and Heeger, Letters to Nature, pp. 477–479, date not given.

Polyaniline as a transparent electrode for polymer light–emitting diodes: Lower operating voltage and higher efficiency, Yang and Heeger, Appl. Phys. Lett. 64(10), Mar. 7, 1994, pp. 1245–1247.

"Inverted" Polymer Light–Emitting Diodes on Cylindrical Metal Substrates, Westerweele, Smith and Heeger, Adv. Mater. 1995, vol. 7, No. 9, pp. 788–790. (no month).

Light emitting diodes based on p–phenylene vinylene oligomer, H. S. Woo, J. G. Lee, H. K. Min, E. J. Oh, Park, K. W. Lee, J. H. Lee, S. H. Cho, T. W. Kim and C. H. Park, Synthetic Metals 71 (1995), pp. 2173. (no month).

Conjugated polymer light–emitting diodes on silicon substrates, Baigent, Marks, Greenham and Friend, Cavendish Laboratoy, Moratti and Holmes, University Chemical Laboratory, Appl. Phys. Lett. 65(21), Nov. 21, 1994, pp. 2636–2638.

Microcavity Effect in a Single–Layer Polymer Light–Emitting Diode, Wittmann, Güner, Friend, Spencer, Moratti, Holmes, Adv. Mater. 1995, vol. 7, No. 6, pp. 541–544.

Photodegradation of poly(p–phenylenevinylene) by laser light at the peak wavelength of electroluminescence, Zyung and Kim, Electronics and Telecommunications Research Insititute, Appl. Phys. Lett. 67(23), Dec. 4, 1995, pp. 3420–3422.

Efficient photodiodes from interpenetrating polymer networks, Halls, Walsh, Greenham, Marseglia, Friend, Moratti, Holmes, Letters to Nature, vol. 376, Aug. 10, 1995, pp. 498–500.

Dual–function semiconducting polymer devices; Light–emitting and photodetecting diodes, Zhang and Heeger, University of California, Appl.Phys. Lett. 64(12), Mar. 21, 1994, pp. 1540–1542.

Charge separation and photovaltaic conversion in polymer composites with internal donor acceptor heterojunctions, Yu and Heeger, University of California, J. Appl. Phys, 78(7), Oct. 1, 1995, pp. 4510–4515.

Poly(p–phenylene vinylene) in Light–Emitting Diodes: Nature of the Lowest Singlet and Triplet Excited States and Effects of Derivatization, Cornil, Beljonne and Bredas, Universite de Mons–Hainaut, pp. 459–460, source and date not given.

Hole–Transporting Compounds for Multi–Layer Polymer Light–Emitting Diodes, Kraft, Burn, Holmes, Synthetic Metals. 55–57 (1993) pp. 4163–4167. (no month).

LEDs Based on Poly(p–phenylenevinyl) and Polyimide LB Films, Wu and Kakimoto, Adv. Mater. vol. 7, No. 9, pp. 812, 814, 1995. (no month).

Poly(p–phenylenevinylene) light–emitting diodes: Enhanced electroluminescent efficiency through charge carrier confinement, Brown, Bradley, Burroughes, Friend, Greenham, Burn, Holmes and Kraft, Appl. Phys, Lett. 61(23), Dec. 7, 1992, pp. 2793–2795.

Electron Transporting Polymers for Light Emitting Diodes, Li, Giles, Grüner, Friend, Holmes and Moratti, , University of Cambridge, pp. 463–464, source and date not given.

Electron injection polymer for polymer light–emitting diodes, Yang and Pei, J. Appl., Phys. 77(9), May 1, 1995, pp. 4807–4809.

1,3,4–Oxadiazole–Containing Polymers as Electron–Injection and Blue Electroluminescent Materials in Polymer Light–Emitting Diodes, Pei and Yang, Chem. Mater. 1995, vol. 7, No. 8., pp. 1568–1575. (no month).

Bright Blue Electroluminscence from an Oxadiazole–Containing Copolymer, Pei and Yang, Adv. Mater. 1995, vol. 7, No. 6, pp. 559–561. (no month).

Design and Application of Electron–Transporting Organic Materials, Strukelj, Papadimitrakopoulos, Miller and Rothberg, Science, vol. 267, Mar. 31, 1995, pp. 1969–1972.

New Organic Electron–Transporting Materials for LEDs Strukelj and Miller, source and date not given, pp. 457–458.

Effects of Polymeric Electron Transporters and the Structure of Poly(p–phenylenevinylene) on the Performance of Light–Emitting Diodes, Strukelj, Miller, Papadimitrakopoulos and Son, J. Am. Chem. Soc. vol. 117 48, 1995, pp. 11976–11983. (no month).

Enhanced Efficiency of Polymer Light Emitting Diodes Utilizing Oxadiazole Polymers, Buchwald, Meier, Karg, Pösch, Schmidt, Strohriegl, Riess and Schwoerer, Adv. Mater. 1995, vol. 7, No. 10, pp. 839–842. (no month).

Poly(p–phenylene vinylene)/tris (8–hydroxy) quinoline aluminum heterostructure light emitting diode, Wu, Chun, Burrows, Sturm, Thompson, Forrest and Register, Princeton University, Appl. Phys. Lett. 66(6) Feb. 6, 1995, pp. 653–655.

Fabrication of self–assembled multilayer heterostructure of poly(p–phenylene vinylene) and its use for an electroluminescent diode, J. Appl. Phys. 78(7), Oct. 1, 1995, pp. 4456–4462.

Degradation and failure of MEH–PPV light–emitting diodes, Scott, Kaufman, Brock, DiPietro, Salem and Goitia, IBM Almaden Research Center, J. Appl. Phys. 79(5), Mar. 1, 1996, pp. 2745–2751.

Alternating–current light–emitting devices based on conjugated polymers, Wang, Gebler, Lin, Blatchford and Jessen, Ohio State University, Epstein, Ohio State University, Appl. Phys. Letter. 68(7), Feb. 12, 1996, pp. 894–896.

Highly efficient electroluminescense of new wide band gap ladder–type poly(para–phenylenes), Tasch Niko, Leising, Scherf, Appl. Phys. Lett. 68(8), Feb. 19, 1996, pp. 1090–1092.

Precursor Route Chemistry and Electronic Properties of Poly(p–phenylene–vinylene), Poly[(2,5–dimethyl–p–phenylene)vinylene] and Poly[(2,5–dimethoxy–p–phenylene)vinylene], Burn, Bradley, Friend, Halliday, Holmes, Jackson and Kraft, J. Chem. Soc. Perkin Trans. 1992, pp. 3225–3231. (no month).

Visible light emission from semiconducting polymer diodes, Braun and Heeger, Appl. Phys. Lett. 58(18), May 6, 1991, pp. 1982–1984.

Fluorinated Poly(p–phenylenevinylene) Copolymers: Preparation and Use in Light–Emitting Diodes, Benjamin, Faraggi, Avny, Davidov and Neumann, Chem. Mater. 1996, vol. 8, No. 2, 1996, pp. 352–355. (no month).

Defect Quenching of Conjugated Polymer Luminescence, Rothberg, Papadimitrakopoulos, Galvin, Miller, Physical Review Letters, vol. 73, No. 5, pp. 744–747, Aug. 1, 1994.

Singlet Oxygen as a Reactive Intermediate in the Photodegradation of an Electroluminescent Polymer, Scurlock, Wang, Ogilby, Sheats and Clough, J. Am. Chem. Soc. 1995, vol. 117, No. 41, pp. 10194–10202. (no month).

Interchain Excitations in Conjugated Polymers, Yan, Rothberg, Kwock and Miller, Physical Review Letters, vol. 75, No. 10, Sep. 4, 1995, pp. 1992–1995.

Spatially Indirect Excitons as Primary Photoexcitations in Conjugated Polymers, Yan, Rothberg, Papadimitrakopoulos, Galvin and Miller, Physical Review Letters, vol. 72, No. 17, Feb. 14, 1994, pp. 1104–1107.

High Peak Brightness Polymer Light–Emitting Diodes, Adv. Mater. 1998, vol. 10, No. 1, pp. 64–68. (no month).

Solid–State Droplet Laser Made from an Organic Blend with a Conjugated Polymer Emitter, Berggren, Dodabalapur, Bao and Slusher, Adv. Mater. 1997, vol. 9, No. 12, pp. 968–971. (no month).

Insoluble Poly[2–(2'–ethylhexyloxy)–5–methoxy–1,4–phenylenevinylene] for Use in Multilayer Light–Emitting Diodes, Burn, Grice, Tajbakhsh, Bradley and Thomas, Adv. Mater. 1997, vol. 9, No. 15, pp. 1171–1174. (no month).

Photo–oxidation of Poly(p–phenylenevinylene), Xing, Johansson, Beamson, Clark, Bredas and Salaneck, Adv. Mater. 1997. vol. 9, No. 13, pp. 1027–1031. (no month).

Theoretical study of geometrical and electronic structures of new π–conjugated poly(arylene) vinylene) analogs, Hong, Kwon and Kim, Synthetic Metals 82 (1996), pp. 183–188. (no month).

Poly(p–phenylenevinylene) by chemical vapor deposition: synthesis, structural evaluation, glass transition, electroluminescence, and photoluminescence, Schäfer, Greiner, Pommerehne, Guss, Vestweber, Tak, Bässler, Schmidt, Lüssem, Schartel, Stümpflen, Wendorff, Spiegel, Möller and Spiess, Synthetic Metals, vol. 82 (1996), pp. 1–9. (no month).

Preparation and optical properties of hybrid sol–gel systems containing doubly anchored oligoarylenevinylenes, Corriu, Hesemann and Lanneau, Chem. Commun. 1996, pp. 1845–1846. (no month).

Chemical vapor deposition of poly (p–phenylenevinylene) based light emitting diodes with low turn–on voltages, Vaeth and Jensen, Appl. Phys. Lett. 71(15), Oct. 13, 1997, pp. 2091–2093.

Chemical Vapor Deposition of Thin Polymer Films Used in Polymer–Based Light Emitting Diodes, Vaeth and Jensen, Adv. Mater. 1997, vol. 9, No. 6, pp. 490–493. (no month).

The Interaction of Poly(p–phenylenevinylene) with Air, Xing, Fahlman, Lögdlund, Santos, Parenté, Lazzaroni, Brédas, Gymer and Salaneck, Adv. Mater. 1996, vol. 8, No. 12, pp. 971–974. (no month).

Microfabrication of an electroluminescent polymer light emitting diode pixel array, Noach, Faraggi, Cohen, Avny, Neumann, Davidov, Lewis, Appl. Phys. Lett. 69(24), Dec. 9, 1996, pp. 3650–3652.

Lasing from conjugated polymer microcavities, Tessler, Denton and Friend, Letters to Nature, vol. 382, Aug. 22, 1996, pp. 695–697.

Indium contamination from the indium–tin–oxide electrode in polymer light–emitting diodes, Schlatmann, Floet, Hilberer, Garten, Smulders, Klapwijk and Hadziioannou, Appl. Phys. Lett. 69(12), Sep. 16, 1996, pp. 1764–1766.

Polyquinoxaline as an excellent electron injecting material for electroluminscent device, Fukuda, Kanabara, Yamamoto, Ishikawa, Takezoe, Fukuda, Appl. Phys. Lett. 68(17), Apr. 22, 1996, pp. 2346–2348.

Exciton diffusion and dissociation in a poly(p–phenylenevinylene)/$C_{60}$ heterojuction photovoltaic cell, J.J.M. Halls, K. Pichler, and R.H. Friend, S.C. Moratti and A.B. Holmes, pp. 3120–3122, Appl. Phys. Lett. 68(22), May 27, 1996.

U.S. Display Industry On the Edge, Ken Werner, pp. 62–69, IEEE Spectrum, May 1995.

Elecroluminscence from poly(phenylene vinylene) in a planar metal–polymer–metal structure, U. Lemmer, D. Vacar, D. Moses, and A.J. Heeger, T. Ohnishi and T. Noguchi, pp. 3007–3310, Appl. Phys. Lett. 68(21), May 24, 1996.

Voltage controlled two color light–emitting electrochemical cells, Yang Yang and Qibing Pei, pp. 2708–2710, Appl. Phys. Lett. 68(19), May 6, 1996.

Efficient, fast response light–emitting electrochemical cells: Electroluminescent and solid electrolyte polymers with interpenetrating network morphology, Yong Cao, Gang Yu, and Alan J. Heeger, C.Y. Yang, pp. 3218–3220, Appl. Phys. Lett. 68(23), Jun. 3, 1996.

Dramatic photoluminescence quenching of phenylene vinylene oligomer thin films upon submonolayer Ca deposition, V. Choong, Y. Park, and T. Gao, T. Wehrmeister and K. Mullen B.R. Hsieh, C.W. Tang, pp. 1492–1494, Appl. Phys. Lett. 69 (10), Sep. 2, 1996.

Charge Injection in Organic Light–Emitting Diodes: Tunneling into low mobility materials, P.S. Davids, Sh. M. Kogan, I.D. Parker, and D.L. Smith, Oct. 7, 1996, pp. 2270–2272, Appl. Phys. Lett. 69(15).

Operating stability of light–emitting polymer diodes based on poly(p–phenylene vinylene), J.C. Carter, I. Grizze, S.K. Heeks, D.J. Lacey, S.G. Latham, P.G. May, O., Ruiz de los Panos, K. Pichler, C.R. Towns, and H.F. Wittmann, pp. 34–36, Appl. Phys. Lett. 71(1), Jul. 7, 1997.

Polymer–light–emitting electrochemical cells with frozen p–i–n junction, Jun Gao, Gand Yu, and Alan J. Heeger, pp. 1293–1295, Appl. Phys. Lett. 71(10), Sep. 8, 1997.

An iodine–doped polymer light–emitting diode, F. Huang and A. G. MacDiarmid, B.R. Hsieh, pp. 2415–2416, Appl. Phys. Lett. 71(17), Oct. 27, 1997.

Novel PPV Derivatives Emitting Light over a Broad Wavelength Range, Prof. J. I. Jin, S.J. Chung, K.K. Kim, 1997, pp. 551–554, Adv. Mater. 9 (7). (no month).

Chiroptical Properties of Poly{2,5–bis[S]–2–methylbutoxy]– 1,4–phenylene vinylene}, Emiel Peeters, Ann Delmotte, Rene A. J. Janssen and E. W. Meijer, 1997, pp. 493–496, Adv. Mater. 9 (6). (no month).

New LEDs Based on Soluble Poly(2,6–Naphthylenevinylene), 1996, pp. 663–666, Adv. Mater. 8(8). (no month).

Efficient Green Electroluminescent Diodes Based on Poly(2–dimethyloctylsily–1,4–phenylenevinylene), 1996, pp. 979–982, Adv. Mater. 8(12). (no month).

Electroluminescence from a soluble poly(p–phenylvinylene) derivative generated using a scanning tunneling microscope, D.G. Lidzey, S.F. Alvarado and P.F. Seidler, A. Bleyer and D.D.C. Bradley, pp. 2008–2010, Appl. Phys. Lett. 71(14), Oct. 6, 1997.

Blue and Green Light Emission from New Soluble Alternating Copolymers Hyun Nam Cho, Dong Young Kim, Young Chul Kim, Jun Young Lee and Chung Yup Kim, 1997, pp. 326–328, Adv. Mater. 9(4). (no month).

Efficient Blue LEDs from a Partially Conjugated Si–Containing PPV Copolymer in a Double–Layer Configuration, Frank Garten, Alain Hilberer, Franco Cacialli, Eddy Esselink, Yvonne van Dam, Bart Schlatmann, Richard H. Friend, Teun M. Klapwiik, and Georges Hadziioannou, 1997, pp. 127–131, Adv. Mater. 9(2). (no month).

Thin film light emitting devices from an electroluminescent ruthenium complex, J.K. Lee, S.D. Yoo, E.X. Handy, and M.F. Rubner, pp. 1686–1688, Appl. Phys. Lett. 69(12), Sep. 16, 1996.

Photoconductivity and charge transporting properties of metal–containing poly(p–phenylenevinylnes)s, Wai Kin Chan, Xiong Gong, and Wai Yue Ng, pp. 2919–2291, Appl. Phys. Lett. 71(20), Nov. 17, 1997.

Highly Oriented Thin Films of a Substituted Oligo (para–phenylenevinylene) on Friction–Transferred PTFE Substrates, Richard E. Gill, Georges Hadziioannou, Phillipe Lang, Francis Garnier, and Jean Claude Wittmann, 1997, pp. 331–334, Adv. Mater. 9(4). (no month).

Ultrafast optical probes of excited states in poly(1,4–phenylene vinylene) and poly(2–fluoro–1,4–phenylene vinylene), Hyo Soon Eom, Sae Chae Jeoung, and Dungho Kim, J.I. Lee and H.K. Shim, C.M. Kim and C.S. Yoon, and K.S. Lim, pp. 563–565, Appl. Phys. Lett. 71(5), Aug. 4, 1997.

Pulsed electroluminescence from organic bilayer light emitting diodes, Y.H. Tak, J. Pommerehne, H. Vestweber, R. Sander, and H. Basler, H.H. Horhold, pp. 1291–1293, Appl. Phys. Lett. 69(9), Aug. 26, 1996.

Photoprocessed and micropatterned conjugated polymer LEDs, D.G. Lidzey, M.A. Pate, M.S. Weaver, T.A. Fisher, D.D.C. Bradley, pp. 141–148, Synthetic Metals 82, 1996. (no month).

Temperature effect on the electronic spectra of poly(p–phenylenevinylene), Jenwei Yu, M. Hayashi, S.H. Lin, K.K. Liang, J.H. Hsu, W.S. Fann, Ching–Ian Chao, Kuen–Ru Chuang, Show–An Chen, pp. 159–166, Synthetic Metals 82, 1996. (no month).

Soluble polypyrrole as the transparent anode in polymer light–emitting diodes, J. Gao, A.J. Heeger, J.Y. Lee, C.Y. Kim, pp. 221–223 Synthetic Metals 82, 1996. (no month). Synthetic Metals 83, 1996. (no month).

Synthesis and spectral properties of poly (arylenevinylenes) incorporating 2–methoxy–5–(2'–ethylhexyloxy)–p–phenylene fragments in the polymer chain, N.N. Barashkov, T.S. Novikova, J.P. Ferraris, pp. 39–46.

Organic–inorganic heterojunction light emitting diodes based on poly(p–phenylene vinylene)/cadmium sulfide thin films, N. Deepak Kumar, Mukesh P. Joshi, Christopher S. Friend, Paras N. Prasad, Ryszard Burzynski, pp. 1388–1390, Appl. Phys. Lett. 71 (10), Sep. 8, 1997.

Enhanced luminance in polymer composite light emitting devices, S.A. Carter, J.C. Scott and P.J. Brock, pp. 1145–1147, Appl. Phys. Lett. 71(9), Sep. 1, 1997.

Ink–jet printing of doped polymers for organic light emitting devices, T.R. Hebner, C.C. Wu, D. March, M.H. Lu, and J.C. Sturm, pp. 519–521, Appl. Phys. Lett. 72(5), Feb. 2, 1998.

Whispering–gallery–mode microring laser using a conjugated polymer, Y. Kawabe, Ch. Spielgelberg, A. Schulzgen, M.F. Nabor, B. Kippelen, E.A. Mash, P.M. Allemand, M. Kuwata–Gonokami, K. Takeda and N. Peyghambarian, pp. 141–143, Appl. Phys. Lett. 72(2), Jan. 12, 1998.

Microlithographic Process for Patterning Conjugated Emissive Polymers, Michelle L. Renak, Guillermo C. Bazan, and Daniel Roitman, 1997, pp. 392–395, Adv. Mater. 9 (5). (no month).

Device model for single carrier organic diodes, P.S. Davids, I.H. Campbell, and D.L. Smith, pp. 6319–6325, J. Appl. Phys. 82 (12), Dec. 15, 1997.

Bipolar charge and current distributions in organic light–emitting diodes, J.C. Scott, S. Karg, S.A. Carter, pp. 1454–1460, J. Appl. Phys. 82(3), Aug. 1, 1997.

Plastic lasers shine brightly, Donal Bradley, Nature vol. 382, Aug. 22, 1996, 1 page.

Planer light–emitting devices fabricated with luminescent electrochemical polyblends, G. Yu, Q. Pei, and A.J. Heeger, pp. 934–936, Appl. Phys. Lett. 70(8), Feb. 24, 1997.

Temperature dependent electron–hole recombination in polymer light–emitting diodes, P.W.M. Blom, M.J.M. de Jong and S. Breedjiik, pp. 930–932, Appl. Phys. Lett. 71 (7), Aug. 18, 1997.

Mapping the confined optical field in a microcavity via the emission from a conjugated polymer D.G. Lidzey and D.D.C. Bradley, M.A. Pate and J.P.R. David, D.M. Whittaker, T.A. Fisher and M.S Skolnick, pp. 744–746, Appl. Phys. Lett. 71(6), Aug. 11, 1997.

Controlling charge injection in organic electronic devices using self–assembled monolayers, I.H. Campbell, J.D. Kress, R. L. Martin, and D.L. Smith, N.M. Barashkov and J.P. Ferraris, pp. 3528–3580, Appl. Phys. Lett. 71 (24), Dec. 15, 1997.

A model for the current–voltage characteristics and the quantum efficiency of single–layer organic light emitting diodes, Y. Kawabe, G.E. Jabbour, S.E. Shaheen, B. Kippelen, and N. Peyghambarian, pp. 1290–1292, Appl. Phys. Lett. 71 (10), Sep. 8, 1997.

A Blue–Emitting Triazole–Based Conjugated Polymer, Alan W. Grice, Ali Tajbakhsh, Paul L. Burn, and Donal D.C. Bradley 1997, pp. 1174–1178, Adv. Mater. 9 (15). (no month).

Device Physics of Polymer Light–emitting Diodes, Paul W.M. Blom, Marc J.M. de Jong and Coen T.H.F. Liedenbaum, ©1998 John Wiley & Sons, Ltd., pp. 390–401, Polymers for Advanced Technologies 9. (no month).

Injection, Transport and Recombination of Charge Carriers in Organic Light–emitting Diodes, Heinz Bassler, ©1998 John Wiley & Sons, Ltd., pp. 402–418, Polymers for Advanced Technologies 9. (no month).

Conjugated Polymer Surfaces and Interfaces in Polymer––based Light–emitting Diodes, W.R. Salaneck and M. Logdland, ©1998 John Wiley & Sons, Ltd., pp. 402–428, Polymers for Advanced Technologies 9. (no month).

Stimulated Emission and Lasing in Conjugated Polymers, U. Lemmer, ©1998 John Wiley & Sons, Ltd., pp. 476–487, Polymers for Advanced Technologies 9. (no month).

Design and Synthesis of Polymers for Light–emitting Diodes, A. Greiner, ©1998 John Wiley & Sons, Ltd., pp. 371–389, Polymers for Advanced Technologies 9. (no month).

Light–emitting Devices Based on Solid Electrolytes and Polyelectrolytes, Dieter Neher, Johannes Gruner, vera Cimrova, Wolfgang Schmidt, Rudy Rulkens and Ulrich Lauter, ©1998 John Wiley & Sons, Ltd., pp. 461–475, Polymers for Advanced Technologies 9. (no month).

Photo–oxidation of Electroluminescent Polymers, B.H. Cumpston and K.F. Jensen, pp. 151–156, Trip, vol. 4, No. 5, May 1996.

Electroluminescent Conjugated Polymers–Seeing Polymers in a New Light, Arno Kraft, Andrew C. Grimsdale, and Andrew B. Holmes, 1998, pp. 403–428, Angew, Chem. Int. Ed. 37. (no month).

Excimer Formation and Luminescence in Conducting Polymers, Esther Conwell, pp. 218–222, Trip, vol. 5, No. 7, Jul. 1997.

Space–charge limited conduction with traps in poly(Phenylene vinylene) light emitting diodes, A. J. Campbell et al., J. Appl. Phys. 82(12), Dec. 15, 1997, pp. 6326–6342.

ac impedance of polymer light–emitting electrochemical cells and light–emitting diodes: a comparative study, Yongfanc Li, Jun Gao, Gang Yu, Yong Cao, Alan J. Heeger, pp. 83–88, Chemical Physics Letters 287, Apr. 1998.

Fluorine Tin Oxide as an Alternative to Indium Tin Oxide in Polymer LEDs, Annica Anderson, Nicklas Johannson, Per Broms, Nu Yu, Donald Lupo, and William R. Salaneck, 1998, pp. 859–863, Adv. Mater. 10(11). (no month).

Thermal Conversion of Poly(paraphenylene–vinylene)Precursor Films: XPS and ESR Studies, T.P. Nguyen, P. Le Rendu, V.H. Tran and P. Molinie, ©1998 John Wiley & Sons, Ltd., pp. 101–106, Polymers for Advanced Technologies 9. (no month).

Tin Oxide as a Cathode in Organic Light–Emitting Diodes, Ana C. Arias, Joaquim R. de Lima, and Ivo A. Hummelgen, 1998, pp. 392–394, Adv. Mater. 10(5). (no month).

Improved–Efficiency Light–Emitting Diodes Prepared from Organic–Soluble PPV and Derivatives with Phenylanthracene and Branched Alkoxy Pendents, Sung–Jae Chung, Jung–II Jim, Chang–Hoon Lee, and Cheoul–Eui Lee, 1998, pp. 684–688, Adv. Mater. 10(9). (no month).

Ultrathin Self–Assembled Layers at the ITO Interface to Control Charge Injection and Electroluminescence Efficiency in Polymer Light–Emitting Diodes, Peter K.H. Ho, Magnus Granstrom, Richard H. Friend, and Neil C. Greenhan, 1998, pp. 769–774, Adv. Mater. 10(10). (no month).

High Peak Brightness Polymer Light–Emitting Diodes, Nir Tessler, Nick T. Harrison, and Richard H. Friend, 1998, pp. 64–68, Adv. Mater. 10(1). (no month).

Light–Emitting Diodes, M. George Craford and Frank M. Steranka, ©1994 VCH Publishers, Inc., pp. 485–515, Encyclopedia of Applied Physics, vol. 8. (no month).

Electroluminescence, Yoshimasa A. Ono, ©1993 VCH Publishers, Inc., pp. 295–326, Encyclopedia of Applied Physics, vol. 5. (no month).

Display manufacturers borrow IC fab methods, Chris Chinnock, Laser Focus World, Sep. 1996, pp. 89–94.

Flat Panel Display Technology, John P. Ziegler and Bruce M. Howard, The Electrochemical Society Interface, pp. 27–32, Summer 1994. (no month).

Fabricating high resolution AMEL flat panel displays, Martin Aguilera, Brad Aitchison, Solid State Technology Nov., 1996, pp. 109–116.

Use of poly(phenyl quinoxaline) as an electron transport material in polymer light–emitting diodes, D. O'Brien, M.S. Weaver, D.G. Lidzey, and D.D.C.. Bradley, pp. 881–883, Appl. Phys. Lett. 69(7), Aug. 12, 1996.

Polymeric light–emitting diodes from molecularly thin poly(3–hexylthiophene) Langmuir–Blodgett films, A.J. Pal. T. Ostergard, J. Paloheimo, and H. Stubb, pp. 1137–1139, Appl. Phys. Lett. 69(8), Aug. 19, 1996.

Integrated three–color organic light–emitting devices, C.C. Wu, J.C. Sturm and R.A. Register, M.E. Thompson, pp. 3117–3119, Appl. Phys. Lett. 69(21), Nov. 18, 1996.

Controlled Spontaneous Emission in Organic Electroluminescent Devices, Noriyuki Takada, Tetsuo Tsutsui, and Shogo Saito, Optoelectronics–Devices and Technologies, vol. 8, No. 3, Sep. 1993, pp. 403–412.

Highly Efficient Light–Emitting Diodes with Microcavities, E.F. Schubert, N.E.J. Hunt, M. Micovic, R.J. Malik, D.L. Sivco, A.Y. Cho, G.J. Zydzik, Science, vol. 265, Aug. 12, 1994, pp. 943–945.

Sol–Gel Synthesis of Hybrid Organic–Inorganic Materials. Hexylene–and Phenylene–Bridged Polysiloxanes, Douglas A. Loy, Gregory M. Jamison, Brigitta M. Baugher, Sharon A. Myers, Roger A. Assink, and Kenneth J. Shea, pp. 656–663, Chem. Mater. 8(3), 1996. (no month).

Electroluminescent zinc sulphide devices produced by sol–gel processing, W. Tang, D.C. Cameron, pp. 221–226, Thin Solid Films 280, 1996. (no month).

Electroluminescence of $TiO_2$ film and $TiO_2:Cu^{2+}$ film prepared by the sol–gel method, Tomoaki Houzouji, Nobuhiro Saito, Akihiko Kudo, Takayoshi Sakata, pp. 109–113, Chemical Physics Letters, 254, May 1996.

Materials for Flat–Panel Displays, J.S. Im and A. Chiang, Guest Editors, MRS Bulletin/March 1996, vol. 21, No. 3, pp. 27–29.

Glass Substrates for Flat Panel Displays, D.M. Moffatt, MRS Bulletin/Mar. 1996, vol. 21, No. 3, pp. 31–34.

Materials in Active–Matrix Liquid–Crystal Displays, J. Hanna and I. Shimizu, MRS Bulletin/Mar. 1996, vol. 21, No. 3, pp. 35–38.

Crystalline Si Films for Integrated Active–Matrix Liquid–Crystal Displays, J.S. Im and R.S. Sposili, MRS Bulletin/Mar. 1996, vol. 21, No. 3, pp. 39–48.

Materials Used in Electroluminexcent Displays, P.D. Rack, A. Naman, P.H. Holloway, S–S. Sun, and R.T. Tuenge, MRS Bulletin/Mar. 1996, vol. 21, No. 3, pp. 49–58.

Diamond–Based Field–Emission Displays, J.E. Jaskie, MRS Bulletin/Mar. 1996, vol. 21, No. 3, pp. 59–64.

Materials and Manufacturing Issues for Color Plasma Displays, L.F. Weber and J.D. Birk, MRS Bulletin/Mar. 1996, vol. 21, No. 3, pp. 65–68.

List of Non–PPV Polymers, 2 pages, source and date not given.

Electroluminescence of Organic Thin Films based on Blends of Polystyrene and Fluorescent Dyes, Peter Fredericksen, Thomas Bjornholm Hans Georg Madsen and Klaus Bechgaard, J. Mater. Chem., 1994, vol. 4, pp. 675–678. (no month).

Electroluminescent devices based on modified polystyrene II. Pendant anthracenyl groups as light emitters, Marcelo Aguiar, Leni Akcelrud, and F.E. Karasz, Synthetic Metals 71, 1995, p. 2189. (no month).

Electroluminescent devices based on modified polystyrene I. Pendant stilbenyl groups as light emitters, Marcelo Aguiar, Leni Akcelrud, and F.E. Karasz, Synthetic Metals 71, 1995, p. 2187. (no month).

Bright blue electroluminescence from poly (N–vinylcarbazole), Juni Kido, Kenichi Hongawa, Katsuro Okuyam, and Katsutoshi Nagai, pp. 2627–2629, Appl. Phys. Lett. 63(19), Nov. 8, 1993.

White light–emitting organic electroluminescent devices using the poly (N–vinylcarbazole) emitter layer doped with three fluorescent dyes, J. Kido, K. Hongawa, K. Okuyama and K. Nagai, pp. 815–817, Appl. Phys. Lett. 64(7), Feb. 14, 1994.

Single–layer white light–emitting organic electroluminexcent devices based on dye–dispersed poly (N–vinylcarbazole), J. Kido, H. Shionoya, and K. Nagai, ©1994 American Institute of Physics, 3 pages, source, date and page numbers not given.

Electroluminescence from Polysilane Film Doped with Europium Complex, Junji Kido, Katsutoshi Nagai, Toshyuki Okamoto, and Terje Skotheim, Chemistry Letters, 1991, pp. 1267–1270. (no month).

Behavior of charge carriers and excitons in multilayer organic light–emitting diodes made from a polysilane polymer as monitored with electroluminescence, Hiroyuki Suzuki and Satoshi Hoshino, NTC Basic Research Laboratories, 8 pages, ©1996, source and page numbers not given.

Poly(methylphenylsilane) film as a hole transport layer in electroluminescent devices, Junji Kido and Katsutoshi Nagai, Yoshiyuki Okamoto, Terje Skotheim, pp. 2760–2762, Appl. Phys. Lett. 59(21), Nov. 18, 1991.

Organic electroluminescent devices based on molecularly doped polymers, Junji Kido and Masafumi Kohda, 3 pages, source, date and page numbers not given.

Polymer Light–Emitting Diodes with Single–and Double Layer Structures Using Poly (2,3–diphenylquinoxaline–5, 8–diyl), Takakazu Yamamto, Tetsuji Inoue and Takaki Kanbara, 4 pages, source, date and page numbers not given.

Efficient blue electroluminescence from a fluorinated polyquinoline, I.D. Parker and Q. Pei, M. Marrocco, pp. 1272–1274, Appl. Phys. Lett. 65 (10), Sep. 5, 1994.

Magnetic resonance in films and photodiodes based on poly–(phenyl–phenylene–vinylene), V. Dyakonov, G. Rosler, and M. Schwoerer, S. Blumstangel and K. Luders, J. Appl. Phys. 79(3), Feb. 1, 1996, pp. 1556–1562.

Efficient blue polymer light–emitting diodes from a series of soluble poly(paraphenylene)s, Y. Yang, Q. Pei, and A.J. Heeger, J. Appl. Phys. 79(2), Jan. 15, 1996, pp. 934–939.

Charge Transport Polymers for Light Emitting Diodes, Xiao–Chang Li, Franco Cacialli, Mark Giles, Johannes Grimer, Richard H. Friend, Andrew B. Holmes, Stephen C. Moratti, and Tuck Mun Yong, Lee, 1995, 898–900, Adv. Mater. 7(11). (no month).

Bright Blue Electroluminescence from and Oxadiazole––Containing Copolymer, Qibing Pei and Yang Yang, 1995, pp. 559–561, Adv. Mater. 7(6). (no month).

Light–Emitting Diodes Based on Copolymer Organic Semiconductors, Danilo Romero, Michael Schaer, Libero Zuppiroli, Bertrand Cesar, Gilles Widawski, and Bernard Francois, 2 pages, source, date and page numbers not given.

Efficient Two Layer LEDs on a Polymer Blend Basis, Jorn Pommerehne, Horst Vestweber, Werner Guss, Rainer F. Hahrt, Heiz Bassler, Michael Porsch and Jorg Daub, 1995, pp. 551–554, Adv. Mater. 7(6). (no month).

Blue emission from polymer light–emitting diodes using non–conjugated polymer blends with air–stable electrodes, C. Zhang, H. von Seggern, B. Kraabel, H.W. Schmidt, A.J. Heeger, pp. 185–188, Synthetic Metals 72, 1995. (no month).

Enhanced electroluminescence from semiconducting polymer blends, G. Yu, H. Nishino, A.J. Heeger, T.–A. Chen. R.D. Rieke, pp. 249–252, Synthetic Metals 72, 1995. (no month).

Electroluminescence from blend films of poly (3–hexylthiophene) and poly (N–vinylcarbazole), H. Nishino, G. Yu, A.J. Heeger, T.A. Chen. and R.D. Rieke, pp. 243–247, Synthetic Metals 68, 1995. (no month).

Synthesis and Liminescent Properties of 2–Phenyl–5–{4 [2–(6–substituent–2H–benz[de]isoquinoline–1, 3(2H)–dione–2–yl) polymethano–]amino–]phenyl–1,3, 4–oxadiazole, Weijuan Ni Jianhau Su, Kongchang Chen, and He Tian, pp. 101–102, Chemistry Letters, 1997. (no month).

Blue photo–and electroluminescence from poly(benzoly–1, 4–phenylene), A. Edwards, S. Blumstengel, I. Sokolik, and R. Dorsinville, H. Tun, T.K. Kwei, and Y. Okamoto, pp. 298–300, Appl. Phys. Lett. 70(3), Jan. 20, 1997.

Green Electroluminescent Emission from Substituted Polyacetylenes, Runguang Sun, Toshio Masuda, and Takayoshi Kobayashi, Jpn. J. Appl. Phys. vol. 35 pp. 1434–1437, Nov. 1, 1996.

Blue Electroluminescence of Substituted Polyacetylenes, Runguang Sun, Toshio Masuda, and Takayoski Kobayashi, Jpn. J. Appl. Phys. vol. 35, pp. 1673–1676, Dec. 15, 1996.

Understanding optical emissions from electrically stressed insulating polymers: electroluminescence in poly(ethylene terephthalate) and poly(ethylene 2,6–naphthalate) films, D. Mary, M. Albertini, and C. Laurent, ©1997 IOP Publishing Ltd., pp. 171–184, source not given. (no month).

Electroluminescent Diodes Utilizing Polysilanes, Akihiko Fujii, Kenji Yoshimoto, Masayoshi Yoshida, Yukata Ohmori, Katsumi Yoshino, Hideki Ueno, Masaya Kaimoto, and Hiroyuki Kojima, Jpn. J. Appl. Phys. vol. 35 pp. 3914–3917, Jul. 1996.

Patterned Emission in Organic Electroluminescent Device Using Photodecomposition of Polysilane Film by UV Light, M. Hiramoto et al. Jpn. J. Appl. Phys. vol. 35, pp. 4809–4812, Sep. 1996.

Room Temperature Ultraviolet Electroluminescence from Evaporated Poly(dimethylsilane) Film, Reiji Hattori, Takeshi Sugano, Junji Shirafuji, and Tsuyoshi Fujiki, Jpn. J. Appl. Phys. vol. 35, pp. 1509–1511, Nov. 1996.

Polysilane–Based Polymer Diodes Emitting Ultraviolet Light, Kenzo Ebihara, Shin–ya Koshihara, Takashi Miyazawa, and Mitsuo Kira, Jpn. J. Appl. Phys. vol. 35, pp. 1278–1280, Oct. 1996.

MicroPatent® Patent Search: Patent List for "cambridge display technology"—Abstracts of 37 patents, Sep. 1998.

MicroPatent® Patent Search: Patent List for "organic electroluminescence"—Abstracts of 82 patents, Sep. 1998.

MicroPatent® Patent Search: Patent List for "organic light emitting" not "organic electroluminescent"—Abstract of 61 patents, Sep. 1991.

MicroPatent® Patent Search: Patent List for "organic luminescent"—Abstract of 241 patents, Sep. 1998.

\* cited by examiner

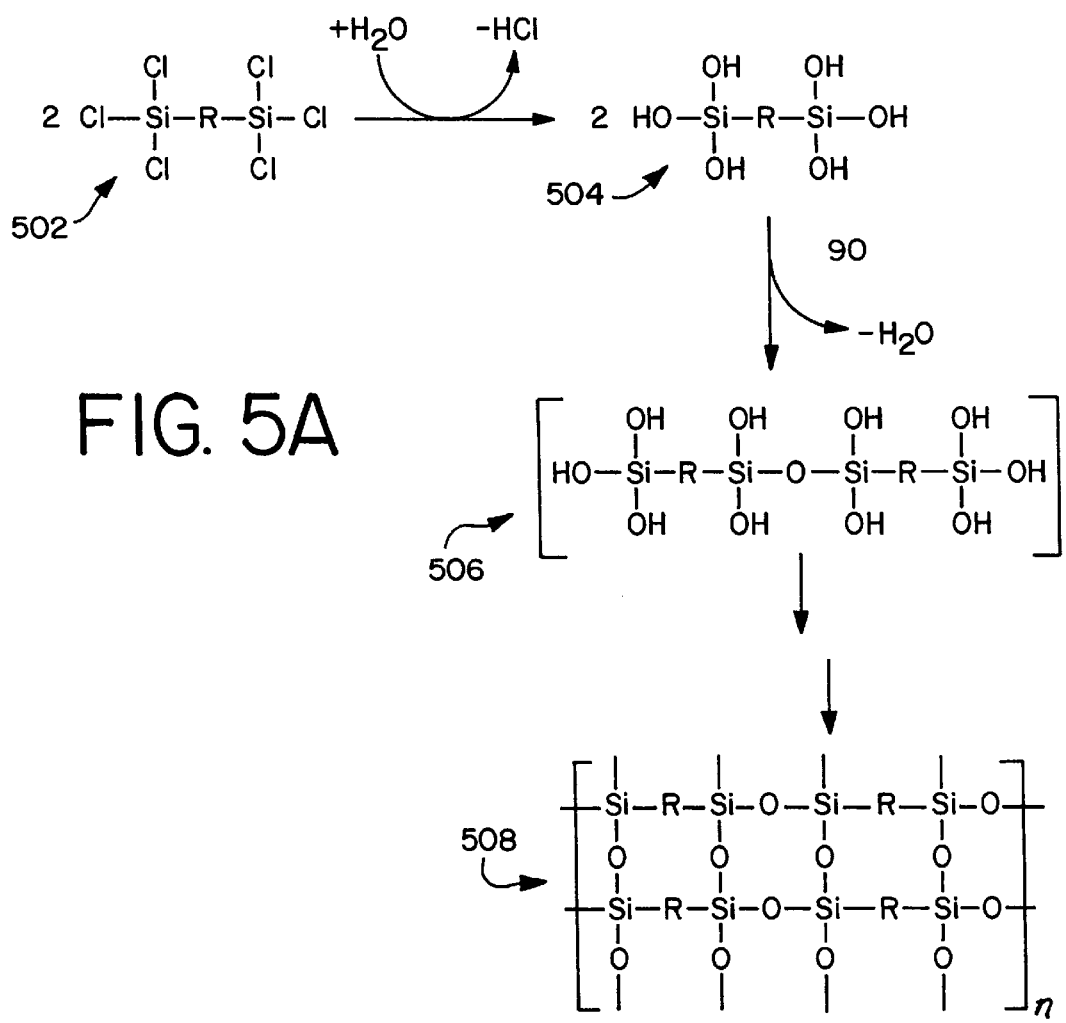
FIG. 5A
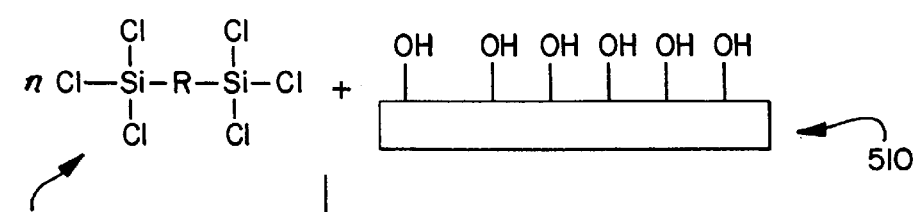
FIG. 5B
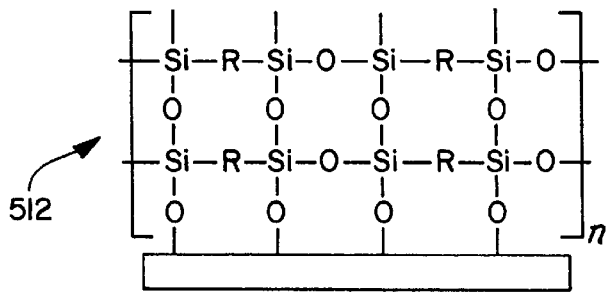

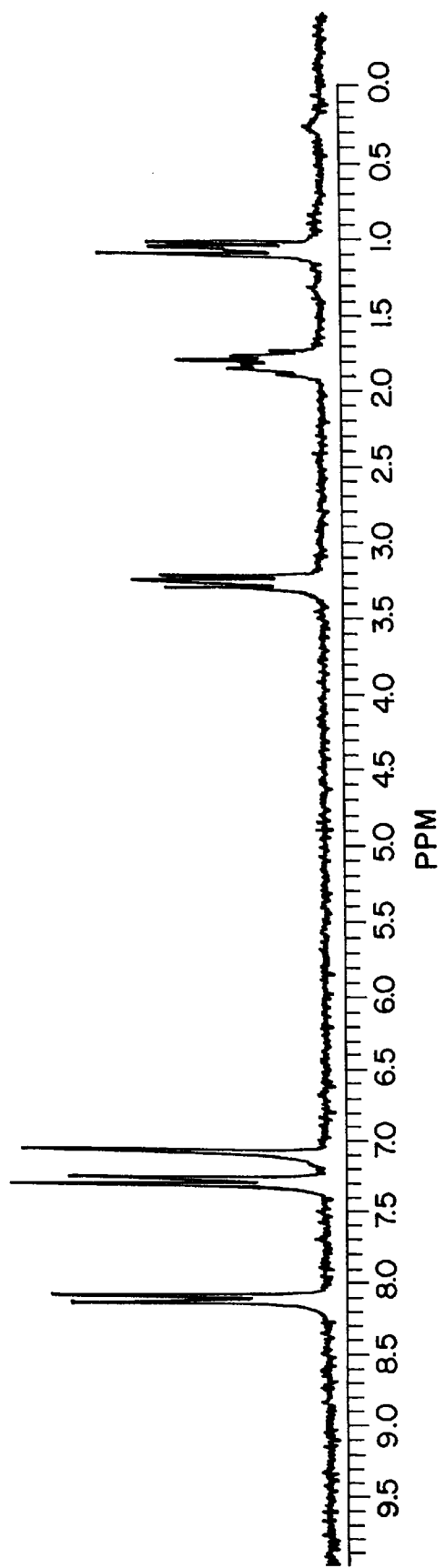

ORGANIC ELECTROLUMINESCENT MATERIALS AND DEVICE MADE FROM SUCH MATERIALS

1 CROSS REFERENCE TO RELATED U.S. PATENT APPLICATIONS

This application claims priority from provisional U.S. patent application Ser. No. 60/081,277, entitled *Organic Electroluminescent Device*, by Homer Chou, filed Apr. 10, 1998. This application is a continuation-in-part of U.S. patent application Ser. No. 09/172,843 entitled *Organic Electroluminescent Materials and Devices Made from Such Materials* and U.S. patent application Ser. No. 09/173,393 entitled *Useful Precursors for Organic Electroluminescent Materials and Devices Made from Such Materials*, both by Homer Chou and both filed on Oct. 15, 1998. Each of these applications is incorporated herein by reference in their entirety and for all purposes.

2 BACKGROUND OF THE INVENTION

2.1 Field of the Invention

The present invention relates to light-emitting materials and devices constructed using such materials. More specifically, the present invention relates to organic, electroluminescent materials and associated devices. The present invention has applications in the areas of materials science, organic chemistry, and electronics.

2.2 The Related Art

Makers of electronic devices that produce visual information, such as computers, are working intensely to develop lightweight display devices that provide brighter, sharper pictures at lower manufacturing cost. The drive to lighter, cheaper, better displays has lead to the development of flat-panel displays ("FPDs") that are commonly used in laptop computers and include a growing share of the desktop computer display market. FPDs are almost exclusively liquid crystal displays ("LCDs"). However, LCD technology has shortcomings, including weak brightness and large power requirements.

One alternative to LCDs are electroluminescent ("EL") displays. EL displays use the luminescense of a solid film that is produced when a voltage is applied to the solid film. Referring to FIG. 1, which illustrates the process generally, the electroluminescent material ("EML") is placed between a cathode and an anode. The application of an electric potential (typically ~100 MV/m) injects holes into the highest occupied molecular orbital ("HOMO") or valence band ("VB") of the EML from the anode, and electrons are injected into the lowest unoccupied molecular orbital ("LUMO") of the EML or conduction band ("CB"). The recombination of the electrons and holes in the EML causes the emission of light from EML.

To increase light output efficiency, a hole transport layer ("HTL") and/or electron transport layer ("ETL") are provided to increase the efficiency of hole (electron) injection and recombination in the EML. This has led to the design of EL displays having the general structure shown in FIG. 2 at 200. There, an electrode 202 is coupled with an electron transport layer 204. ETL 204 is coupled with electroluminescent layer 206, which, in turn, is coupled with hole transport layer 208. HTL 208 is coupled with electrode 210. Electrodes 202 and 210 are connected by contacts 212 and 214 that are each coupled to a source 216.

Presently, EL displays are fabricated using either inorganic materials, such as manganese (Mn)-doped zinc sulfide (ZnS), or organic materials such as polyphenylene vinylene ("PPV") and its derivatives. However, no satisfactory EL material has been developed for widespread applications.

Although inorganic EL displays can provide high performance and durability, they suffer from large power requirements and expensive, low-throughput fabrication processes. Thus, inorganic EL displays have been relegated largely to niche applications, such as military and medical applications. Organic EL displays, on the other hand, can be fabricated more cheaply and simply than inorganic EL displays, but suffer from relatively poor performance.

Thus, a need remains to provide an EL display having a cost/performance profile that is suitable for the general marketplace. Such a device will require materials that are relatively inexpensive and simple to prepare compared to inorganic EL displays while providing comparable performance characteristics. The present invention meets these and other needs.

SUMMARY OF THE INVENTION

The present invention provides organic electroluminescent materials having desirable efficiency, weight, and durability properties, as well as devices made from such materials. The materials provided by the present invention are relatively straightforward to make, thereby being economically attractive. In addition, the light-emitting organic materials of the invention have been found to have performance characteristics comparable to inorganic light-emitting devices. Thus, the organic electroluminescent materials and devices of the invention will be appreciated by those of skill in the materials and electronics arts to address important needs in those fields.

In a first aspect, the present invention provides an electroluminescent device. The device of the invention includes, in one embodiment, an anode and a cathode. An organic electroluminescent material is electroluminescently conductively coupled directly with the anode and cathode such that the organic electroluminescent material emits light upon the application of a voltage across the anode and cathode. The organic electroluminescent material includes an organo-siloxane polymer. The main chain of the organo-siloxane polymer comprises an organic component that can be chosen from the group alkenyl, alkynyl, aralkyl, aryl, heteroaralkyl, and heteroaryl, and which can be substituted with hydrogen, alkyl, aryl, heteroalkyl, heteroaralkyl, nitro, cyano, hydroxy, alkoxy, aryloxy, thio, alkythio, arylthio, amino, halogen, dialkylamino, diarylamino, diaralkylamino, arylamino, alkylamino, arylalkylamino, carbonyloxy, carbonylalkoxy, carbonylalkyloxy, alkylcarbonyloxy, arylcarbonyloxy, alkoxylcarbonyloxy, sulfonyl, or sulfonyloxy. The organic component includes at least two covalent bonds coupling the organic component to the main chain of the organo-siloxane polymer.

In one embodiment, the organic component is selected from the group consisting of alkylene, aralkylene, arylene, heteroaralkylene, and heteroarylene. In a more specific embodiment, the organic component is arylene or heteroarylene, and, still more specifically, arylene. More particular embodiments include those for which the organic component comprises a polycyclic aromatic carbon network containing between 2 and 7 fused aromatic rings. Still more particular embodiments are those for which the polycyclic ring system is selected from the group consisting of electroluminescent agents, hole transport agents, electron transport agents, and combinations thereof.

In some embodiments, the organic component is a polycyclic aromatic carbon ring system that functions as an electroluminescent agent. In a more specific embodiment, the organic component comprises anthracene. In a still more specific embodiment, the anthracene is coupled with a silicon atom in the main chain of the organo-siloxane polymer by at least one alkyl group. In one embodiment, the alkyl group has the formula —CH$_2$(CH$_2$)$_m$CH$_2$—, where m is an integer between 0 and 4. In another more specific embodiment, the anthracene is coupled with the main chain of the organo-siloxane polymer by two such alkyl groups. The alkyl groups can be situated at two symmetric positions on the anthracene. A specific example of one such substituted anthracene is that for which m is 1 and the alkyl groups are located at the opposing central carbon atoms of the anthracene molecule: 9,10-bis(trimethylene)anthracene:

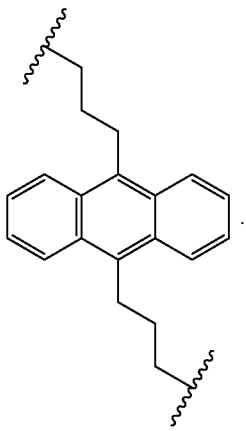

In another embodiment, the organic component comprises pentacene. In a still more specific embodiment, the pentacene is coupled with a silicon atom in the main chain of the organo-siloxane polymer by at least one alkyl group. In one embodiment, the alkyl group has the formula —CH$_2$(CH$_2$)$_m$CH$_2$—, where m is an integer between 0 and 4. In another more specific embodiment, the pentacene is coupled with the main chain of the organo-siloxane polymer by two such alkyl groups, which alkyl groups can be situated at symmetric positions on the carbon ring system. A specific example of one such substituted pentacene is that for which m is 1: 6,13-bis(trimethylene)pentacene:

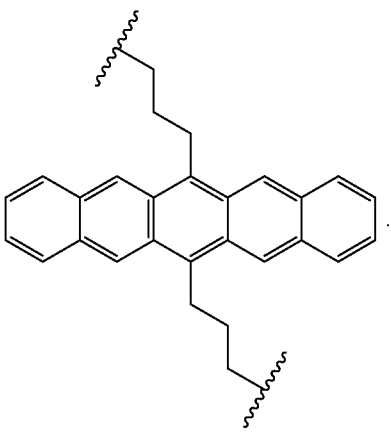

The electroluminescent material can further include a dopant, such as an electron transport material, a hole transport material, or a dye. The electron transport material, hole transport material, or dye can be provided individually or in combination. In one embodiment, the hole transport material can be, without limitation, a porphyrin or aromatic tertiary amine. In another embodiment, the dye can be, without limitation, coumarin, a rhodamine salt (e.g., rhodamine perchlorate), or perylene. In still another embodiment, the organo-siloxane polymer is cross-linked with oxygen atoms.

In another aspect, the invention provides an organic electroluminescent material comprising an organo-siloxane polymer in combination with an electron transport material, a hole transport material, or a dye. The electron transport material, hole transport material, or dye can be combined with the organo-siloxane polymer individually or in combination. The organic component of the organo-siloxane polymer is selected from the group consisting of alkenyl, alkynyl, aralkyl, aryl, heteroaralkyl, and heteroaryl, which can substituted optionally with hydrogen, alkyl, aryl, heteroalkyl, heteroaralkyl, nitro, cyano, hydroxy, alkoxy, aryloxy, thio, alkythio, arylthio, amino, halogen, dialkylamino, diarylamino, diaralkylamino, arylamino, alkylamino, arylalkylamino, carbonyloxy, carbonylalkoxy, carbonylalkyloxy, alkylcarbonyloxy, arylcarbonyloxy, alkoxylcarbonyloxy, sulfonyl, or sulfonyloxy. The organic component includes at least two covalent bonds coupling the organic component with the main chain of the organo-siloxane polymer.

In a more specific embodiment, the organic component comprises anthracene. In a still more specific embodiment, the anthracene is coupled with a silicon atom in the main chain of the organo-siloxane polymer by at least one alkyl group. In one embodiment, the alkyl group has the formula —CH$_2$(CH$_2$)$_m$CH$_2$—, where m is an integer between 0 and 4. In another more specific embodiment, the anthracene is coupled with the main chain of the organo-siloxane polymer by two such alkyl groups. The alkyl groups can be situated at two symmetric positions on the anthracene. A specific example of one such substituted anthracene is that for which m is 1 and the alkyl groups are located at the opposing central carbon atoms of the anthracene molecule: 9,10-bis(trimethylene)anthracene.

In another embodiment, the organic component comprises pentacene. In a still more specific embodiment, the pentacene is coupled with a silicon atom in the main chain of the organo-siloxane polymer by at least one alkyl group. In one embodiment, the alkyl group has the formula —CH$_2$(CH$_2$)$_m$CH$_2$—, where m is an integer between 0 and 4. In another more specific embodiment, the pentacene is coupled with the main chain of the organo-siloxane polymer by two such alkyl groups, which alkyl groups can be situated at symmetric positions on the carbon ring system. A specific example is 6,13-bis(trimethylene)pentacene.

In one embodiment, a hole transport material is included with the organic electroluminescent material. In one embodiment, the hole transport material can be, without limitation, a porphyrin or aromatic tertiary amine. In another embodiment, a dye is included with the organic electroluminescent material. The dye can be, without limitation, coumarin, a rhodamine salt (e.g., rhodamine perchlorate), or perylene. In still another embodiment, the organo-siloxane polymer is cross-linked with oxygen atoms.

In another aspect, the present invention provides an organo-siloxane polymer having a main chain including silicon, oxygen, and an organic component selected from alkenyl, alkynyl, aralkyl, aryl, heteroaralkyl, and heteroaryl. The organic component can be substituted optionally with hydrogen, alkyl, aryl, heteroalkyl, heteroaralkyl, nitro, cyano, hydroxy, alkoxy, aryloxy, thio, alkythio, arylthio, amino, halogen, dialkylamino, diarylamino, diaralkylamino, arylamino, alkylamino, arylalkylamino, carbonyloxy, carbonylalkoxy, carbonylalkyloxy, alkylcarbonyloxy, arylcarbonyloxy, alkoxylcarbonyloxy, sulfonyl, or sulfonyloxy. The organic component includes at least two covalent bonds coupling the organic component to the main chain of the organo-siloxane polymer.

In a more specific embodiment, the organic component comprises anthracene. In a still more specific embodiment, the anthracene is coupled with a silicon atom in the main chain of the organo-siloxane polymer by at least one alkyl group. In one embodiment, the alkyl group has the formula —$CH_2(CH_2)_mCH_2$—, where m is an integer between 0 and 4. In another more specific embodiment, the anthracene is coupled with the main chain of the organo-siloxane polymer by two such alkyl groups. The alkyl groups can be situated at two symmetric positions on the anthracene. A specific example of one such substituted anthracene is that for which m is 1 and the alkyl groups are located at the opposing central carbon atoms of the anthracene molecule: 9,10-bis (trimethylene)anthracene.

In another embodiment, the organic component comprises pentacene. In a still more specific embodiment, the pentacene is coupled with a silicon atom in the main chain of the organo-siloxane polymer by at least one alkyl group. In one embodiment, the alkyl group has the formula —$CH_2(CH_2)_mCH_2$—, where m is an integer between 0 and 4. In another more specific embodiment, the pentacene is coupled with the main chain of the organo-siloxane polymer by two such alkyl groups, which alkyl groups can be situated at symmetric positions on the carbon ring system. A specific example is 6,13-bis(trimethylene)pentacene.

In still another aspect, the present invention provides a method for fabricating an electroluminescent device in which an anode and a cathode are provided. The anode and cathode are coupled with an organic electroluminescent material that includes silicon-oxygen bonds under conditions effective to allow direct, electroluminescent conduction among the organic electroluminescent material, anode, and cathode such that the organic electroluminescent material emits light upon application of a voltage across the anode and cathode. Thus, the unique cross-linked organo-siloxane material provided by the present invention enables the production of more efficient and robust electroluminescent devices.

These and other aspects and advantages will become apparent when the Description below is read in conjunction with the accompanying Drawings.

4 BRIEF DESCRIPTION OF THE DRAWINGS

FIG. 1 is a schematic of the electronic energy levels for an electroluminescent device comprising an anode, a hole transport layer ("HTL"), an electroluminescent layer ("EML"), and electron transport layer ("ETL"), and a cathode. Also shown are the conduction bands ("CB") and valence bands ("VB") of the materials. The filled circles represent LUMOs (lowest unoccupied molecular orbitals); the empty circles represent HOMOs (highest occupied molecular orbitals).

Figure 1:
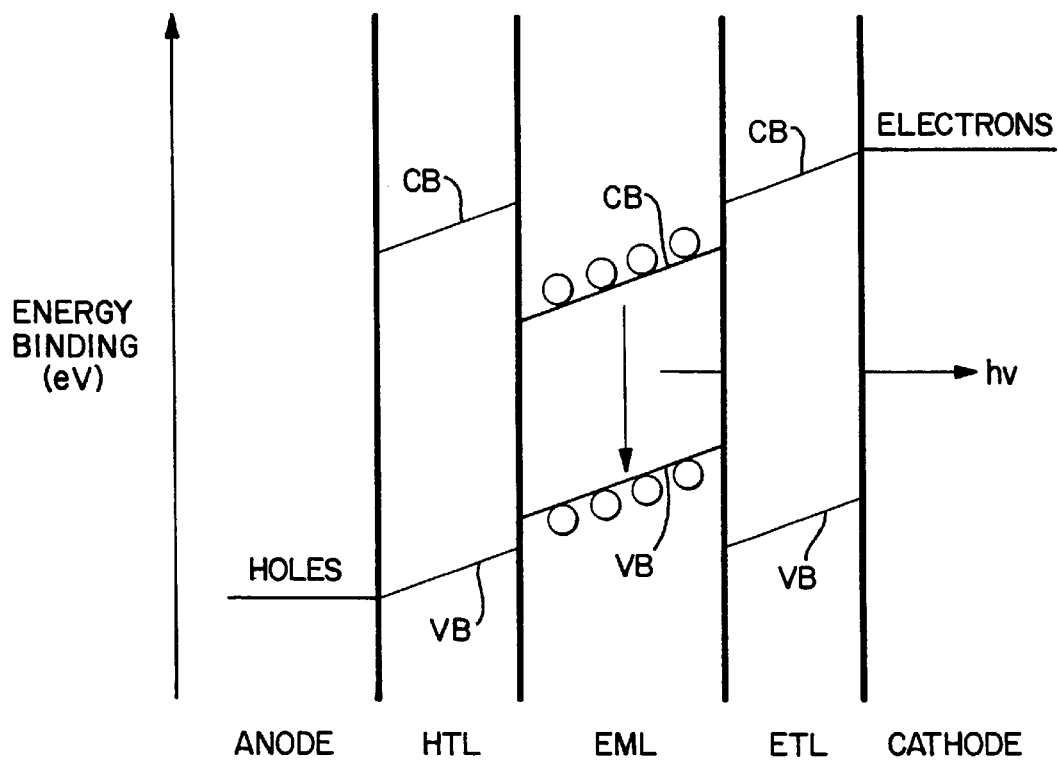
Figure 2:
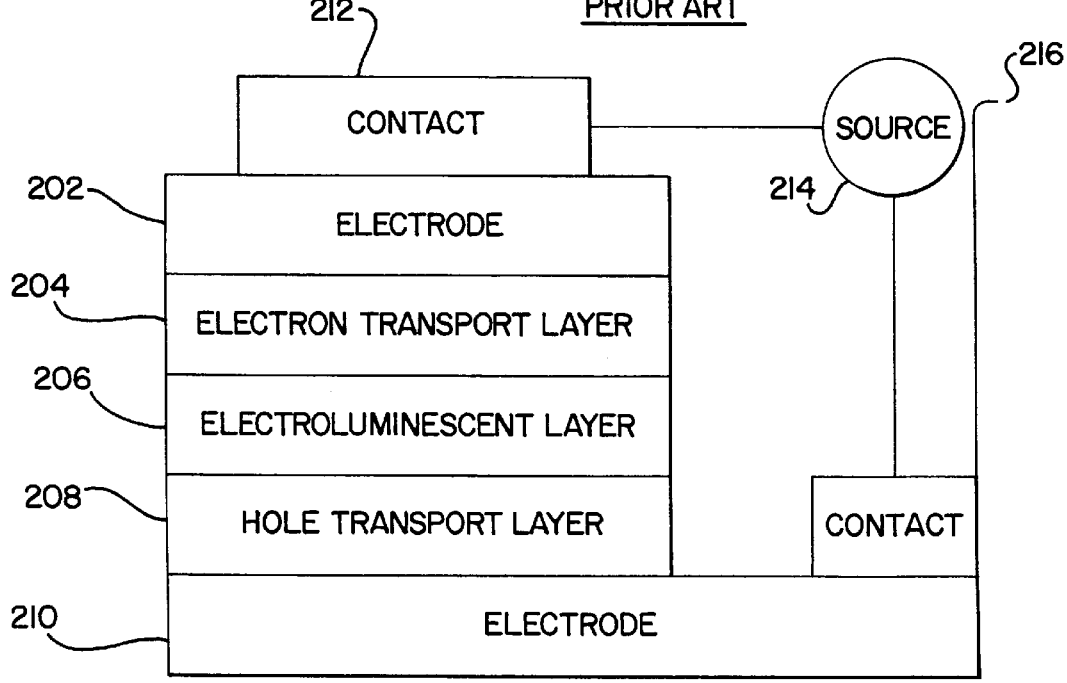
FIG. 2 is a schematic of an electroluminescent device according to the prior art that is consistent with the energy diagram illustrated in FIG. 1.

FIG. 5A and FIG. 5B are schematics describing the formation of various siloxane networks in accordance with the present invention. FIG. 5A is a schematic illustration of a proposed chemical reaction mechanism by which the organo-siloxane polymers of the invention are formed. FIG. 5B illustrates a proposed chemical reaction mechanism for the formation of substrate-bound organo-siloxane polymers of the invention.

FIG. 6 is the proton nuclear magnetic resonance spectrum ("$^1$H NMR") of 9,10-bisallylanthracene taken at an applied field strength of 200 megahertz (MHz) using a hexadeuterobenzene ($C_6D_6$) standard.

5 DESCRIPTION OF SOME EMBODIMENTS OF THE INVENTION

The present invention provides organic electroluminescent materials having desirable efficiency, weight, and durability properties, as well as devices made from such materials. The materials provided by the present invention are relatively straightforward to make, thereby being economically attractive. These beneficial results are achieved in some embodiments in which a single electroluminescent conductive layer replaces the multiplicity of layers used by the prior art. Thus, the organic electroluminescent materials and devices of the invention will be appreciated by those of skill in the materials and electronics arts to address important needs in those fields.

5.1 Definitions

The following terms will be understood as defined in this Section 5.1 unless noted otherwise.

5.1.1 Electroluminescent Material

A material that emits photons under the application of an electric potential. The photons emitted can have any energy, including energy in the range of the visible, ultraviolet (UV), and infra red portions of the electromagnetic spectrum.

5.1.2 Electroluminescent Article

A device including at least an anode, a cathode, and an electroluminescent material arranged between the anode and cathode.

5.1.3 Conducting Material

A "conducting material" as used herein means a material that allows the passage of electrons under the application of an electric potential of less than about 10 volts/micrometer (V/$\mu$m).

5.1.4 Electroluminescently Conductively Coupled Directly

The phrase "electroluminescently conductively coupled directly" as used herein means an arrangement of an electrode and an electroluminescent material in which electrons move from the electrode to a electroluminescent material without traversing an unenhanced hole transport material or unenhanced electron transport material (as defined with respect to Sections 5.1.5–5.1.8 hereinbelow) that is arranged between the electroluminescent material and the electrode.

5.1.5 Hole Transport Layer ("HTL")

A "hole transport layer" ("HTL") is a material that stabilizes the formation of radical cations in an electroluminescent article containing a certain electroluminescent material relative to the same electroluminescent article lacking such a material. Examples of hole transport layers include, without limitation, substituted and unsubstituted phthalocyanic and porphyrinic compounds such as described in U.S. Pat. No. 5,409,783, which is incorporated herein by reference, such as silicon phthalocyanine dichloride and 5,10,15,20-tetraphenyl-21H,23H-porphine silicon (IV) dichloride. Other examples of HTLs include, without limitation, tertiary aromatic amines such as those described in U.S. Pat. Nos. 3,180,730; 3,567,450; and 3,658,520 (each of which is incorporated herein by reference); as well as the above-incorporated U.S. Pat. No. 5,409,783.

5.1.6 Enhanced Hole Transport Layer

An "enhanced hole transport layer" is defined herein to mean a hole transport layer as defined in Section 5.1.5 that further includes at least one additional component that increases the performance of the electroluminescent article relative to an electroluminescent article lacking an enhanced hole transport layer as measured by performance characteristics including, but not limited to, threshold turn-on voltage, luminosity (brightness), article lifetime, and emission wavelength(s).

5.1.7 Electron Transport Layer ("ETL")

An "electron transport layer" ("ETL") is a material that stabilizes the formation of radical anions in an electroluminescent article containing a certain electroluminescent material relative to the same electroluminescent article lacking such a material. Exemplary ETL materials include, without limitation, substituted oxazoles, isoxazoles, thiazoles, isothiazoles, oxadiazoles, and thiadiazoles, such as those described in U.S. Pat. No. 5,276,381, which is incorporated herein by reference.

5.1.8 Enhanced Electron Transport Layer

An "enhanced electron transport layer" is an electron transport layer as defined in Section 5.1.7 that further includes at least one additional component that increases the performance of the electroluminescent article relative to an electroluminescent article lacking an enhanced electron transport layer as measured by performance characteristics including, but not limited to, threshold turn-on voltage, luminosity (brightness), article lifetime, and emission wavelength(s).

5.1.9 Alkyl

The term "alkyl" as used herein refers to a straight, branched, or cyclic hydrocarbon chain fragment or radical containing between about one and about twenty carbon atoms, more preferably between about one and about ten carbon atoms (e.g., methyl, ethyl, n-propyl, iso-propyl, cyclopropyl, n-butyl, iso-butyl, tert-butyl, cyclobutyl, adamantyl, noradamantyl and the like). Straight, branched, or cyclic hydrocarbon chains having eight or fewer carbon atoms will also be referred to herein as "lower alkyl". The hydrocarbon chains may further include one or more degrees of unsaturation, i.e., one or more double or triple bonds (e.g., vinyl, propargyl, allyl, 2-buten-1-yl, 2-cyclopenten-1-yl, 1,3-cyclohexadien-1-yl, 3-cyclohexen-1-yl and the like). Alkyl groups containing double bonds such as just described will also be referred to herein as "alkenes". Similarly, alkyl groups having triple bonds will also be referred to herein as "alkynes". However, as used in context with respect to cyclic alkyl groups, the combinations of double and/or triple bonds do not include those bonding arrangements that render the cyclic hydrocarbon chain aromatic.

In addition, the term "alkyl" as used herein further includes one or more substitutions at one or more carbon atoms of the hydrocarbon fragment or radical. Such substitutions include, but are not limited to: aryl; heterocycle; halogen (defined herein to include fluoro (—F), chloro (—Cl), bromo (—Br), and iodo (—I)), to form, e.g., trifluoromethyl, —CF$_3$; nitro (—NO$_2$); cyano (—CN); hydroxyl (also referred to herein as "hydroxy"), alkoxyl (also referred herein as alkoxy) or aryloxyl (also referred to herein as "aryloxy", —OR); thio or mercapto, alkyl, or arylthio (—SR); amino, alkylamino, arylamino, dialkyl- or diarylamino, or arylalkylamino (—NRR'); aminocarbonyl, alkylaminocarbonyl, arylaminocarbonyl, dialkylaminocarbonyl, diarylaminocarbonyl or arylalkylaminocarbonyl (—C(O)NRR'); carboxyl, or alkyl- or aryloxycarbonyl (—C(O)OR); carboxaldehyde, or aryl- or alkylcarbonyl (—C(O)R); iminyl, aryl- or alkyliminyl (—C(=NR)R'); sulfo (—SO$_2$OR); alkyl- or arylsulfonyl (—SO$_2$R); carbamido (—HNC(=O)NRR'); or thiocarbamido (—HNC(=S)NRR'); trihalosilyl (X$_3$Si—, where X is halogen as defined herein); trialkoxysilyl ((RO$_3$Si—)); where R and R' independently are hydrogen, aryl or alkyl as defined herein. Substituents including heterocyclic groups (i.e., heterocycle, heteroaryl, and heteroaralkyl) are defined by analogy to the above-described terms. For example, the term "heterocycleoxy" refers to the group —OR, where R is heterocycle as defined below.

5.1.10 Alkenyl

The term "alkenyl" refers to an alkene as defined in Section 5.1.9 above in which two valences of the alkene are used to join the alkene to the main chain of the organo-siloxane polymer of the invention.

5.1.11 Alkynyl

The term "alkynyl" refers to alkynes as defined in Section 5.1.9 above in which two valences of the alkyne are used to join the alkyne to the main chain of the organo-siloxane polymer of the invention.

5.1.12 Carbonyl

The term "carbonyl" as used herein refers to the functional group —C(O)—. However, it will be appreciated that this group may be replaced with well-known groups that have similar electronic and/or steric character, such as thiocarbonyl (—C(S)—); sulfinyl (—S(O)—); sulfonyl (—SO$_2$—); phosphonyl (—PO$_2$—), and methylene (—C(CH$_2$)—). Other carbonyl equivalents will be familiar to those having skill in the medicinal and organic chemical arts.

5.1.13 Aryl

The term "aryl" as used herein refers to cyclic aromatic hydrocarbon chains having twenty or fewer carbon atoms, e.g., phenyl, naphthyl, biphenyl and anthracenyl. One or more carbon atoms of the aryl group may also be substituted with, e.g.,: alkyl; aryl; heterocycle; halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; carboxaldehyde, or aryl- or alkylcarbonyl; iminyl, or aryl- or alkyliminyl; sulfo; alkyl- or arylsulfonyl; hydroximinyl, or aryl- or alkoximinyl; carbamido; or thiocarbamido. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heterocycleoxy, heteroaryloxy, and heteroaralkylthio) are defined by analogy to the above-described terms.

5.1.14 Aralkyl

The term "aralkyl" as used herein refers to an aryl group that is joined to a parent structure by an alkyl group as described above, e.g., benzyl, α-methylbenzyl, phenethyl, and the like.

5.1.15 Heterocycle

The term "heterocycle" as used herein refers to a cyclic alkyl group or aryl group as defined above in which one or more carbon atoms have been replaced by a non-carbon atom, especially nitrogen, oxygen, or sulfur. Non-aromatic heterocycles will also be referred to herein as "cyclic heteroalkyl". Aromatic heterocycles are also referred to herein as "heteroaryl". For example, such groups include furyl, tetrahydrofuryl, pyrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridazinyl, triazinyl, piperidinyl, morpholinyl, thiomorpholinyl, pyrazinyl, piperazinyl, pyrimidinyl, naphthyridinyl, benzofuranyl, benzothienyl, indolyl, indolinyl, indolizinyl, indazolyl, quinolizinyl, quinolinyl, isoquinolinyl, cinnolinyl, phthalazinyl, quinazolinyl, quinoxalinyl, pteridinyl, quinuclidinyl, carbazolyl, acridiniyl, phenazinyl, phenothiazinyl, phenoxazinyl, purinyl, benzimidazolyl, benzthiazolyl, and benzoxazolyl.

The above heterocyclic groups may further include one or more substituents at one or more carbon and/or non-carbon atoms of the heteroaryl group, e.g.: alkyl; aryl; heterocycle; halogen; nitro; cyano; hydroxyl, alkoxyl or aryloxyl; thio or mercapto, alkyl- or arylthio; amino, alkyl-, aryl-, dialkyl-diaryl-, or arylalkylamino; aminocarbonyl, alkylaminocarbonyl, arylarninocarbonyl, dialkylaminocarbonyl, diarylaminocarbonyl or arylalkylaminocarbonyl; carboxyl, or alkyl- or aryloxycarbonyl; carboxaldehyde, or aryl- or alkylcarbonyl; iminyl, or aryl- or alkyliminyl; sulfo; alkyl- or arylsulfonyl; hydroximinyl, or aryl- or alkoximinyl; carbamido; or thiocarbamido. In addition, two or more alkyl substituents may be combined to form fused heterocycle-alkyl or heterocycle-aryl ring systems. Substituents including heterocyclic groups (e.g., heterocycleoxy, heteroaryloxy, and heteroaralkylthio) are defined by analogy to the above-described terms.

5.1.16 Heterocyclealkyl

The term "heterocyclealkyl" refers to a heterocycle group that is joined to a parent structure by one or more alkyl groups as described above, e.g., 2-piperidylmethyl, and the like. The term "heteroaralkyl" as used herein refers to a heteroaryl group that is joined to a parent structure by one or more alkyl groups as described above, e.g., 2-thienylmethyl, and the like.

5.2 Electroluminescent Devices

In another aspect, the present invention provides electroluminescent devices. In one embodiment, shown in FIG. 3, an organic electroluminescent device comprises first and second electrodes 302, 304 and a single conductive electroluminescent layer 306 that is electroluminescently conductively coupled directly with the first and second electrodes. In a more particular embodiment, electroluminescent layer 306 is comprised of an organic electroluminescent material that includes silicon-oxygen bonds and is described in greater detail in Section 5.3 below. In a more particular embodiment, the first electrode is a cathode and the second electrode is an anode. Electric contacts 308 and 310 can be attached to the electrodes. Finally, the entire device can be driven by an electrical source 312. Another embodiment, shown FIG. 4, comprises first electrode 402, second electrode, 404, a conductive light-emitting layer 406 that is electroluminescently conductively coupled directly with the first and second electrodes. Electric contacts 408 and 410, and an electrical source 412. In this embodiment, a substrate 414 is coupled with electrode 402.

The electrode can be made from any materials known in the electronics and solid state device arts for making electrodes. Such materials can be selected from electrically conductive metals (such as gold (Au), silver (Ag), copper (Cu), aluminum (Al), indium (In), magnesium (Mg), sodium (Na), potassium (K), and the like), or alloys of these electrically conductive metals (such as Mg—Ag, and Mg—In). Useful electrode materials also include conducting oxides (e.g., zinc oxide, stannic oxide, indium oxide, ITO (indium tin oxide), or conducting composite materials (e.g., silver-containing borosilicate glass, silver-containing epoxy resins, silicon rubber, and lithium fluoride (LiF)-containing aluminum (Al)). Still other materials will be familiar to those of skill in the electronics and solid-state device arts. If the first electrode is also to be used as a light-emitting surface, an electrode material such as ITO or gold can be used to increase the transmittance of light emitted from the luminescent layer. Deposition thicknesses of between about 10 nanometers (nm) and about 1000 nm may be used. More specific thicknesses include those between about 50 nm and about 500 nm. Still more specific thicknesses are those between about 100 nm and about 400 nm. Even more specific thicknesses include those between about 200 nm and about 300 nm.

The first electrode may act as the anode or the cathode. In one embodiment, if the first electrode is used as the anode, then the second (opposite) electrode is fabricated from an electrically conductive material having work function larger than the work function of the first electrode. Conversely, if the first electrode is used as the cathode, then the second (opposite) electrode is made from an electrically conductive material having a work function smaller than the work function first electrode. In more specific embodiments, the anode has a work function of at least about 4 electron volts ("eV"); and the cathode material has a work function of less than about 4 eV.

The first electrode can be formed using any of the techniques known in the art of fabricating solid-state electronic devices. Examples of such methods include, but are not limited to, the following. Physical vapor deposition, including resistance heating, electron beam heating, high frequency induction heating, reactive vapor deposition, molecular beam epitaxy, hot wall vapor deposition, ion plating, or ionized cluster beam methods. Sputtering methods, including diode sputtering, diode magnetron sputtering, triode and tetrode plasma sputtering, reactive sputtering, ionized beam sputtering, and combinations of such methods. Casting methods, in which a precursor molecule is dissolved in an appropriate solvent (e.g., chloroform, tetrahydrofuran, benzene, toluene, xylene, or mesitylene) and then cast onto a surface to create a film. The film can be further hardened by placing the device in an oven (under vacuum or a controlled atmosphere) for 10 minutes–24 hours at 30° C.–100° C. Spin casting, in which a suitable amount of a solution as described for casting is dropped onto a surface. The surface is rotated at about 100 revolutions-per-minute ("rpm")–about 20,000 rpm for a period of between about 5 seconds ("s") and about 200 s. The resulting film is then dried as described. These steps can be repeated using different solutions to form a laminate structure. The amounts of materials, solutions, methods for deposition will depend on various factors well-known among those of skill in the solid-state electronic device arts.

The second electrode can be formed using the methods and materials just described with respect to the first electrode. In one embodiment, the second electrode is formed directly on the electroluminescent layer. In one embodiment, the second electrode is effective to prevent substantially any crystallization of the electroluminescent layer such that the layer retains a substantially amorphous structure that reduces any natural quenching of the layer's luminescence during operation of the device.

In some embodiments, a substrate is included. In one embodiment, the substrate comprises a substantially transparent or substantially semi-transparent to allow light created by the organic light emitting material to be emitted from the device. Examples of suitable materials include glass, plastic, quartz, ceramic, and silicon. The choice of materials and methods of fabrication will be familiar among those of skill in the solid-state device and electronics arts.

5.3 Organic Electroluminescent Materials

Figure 3:
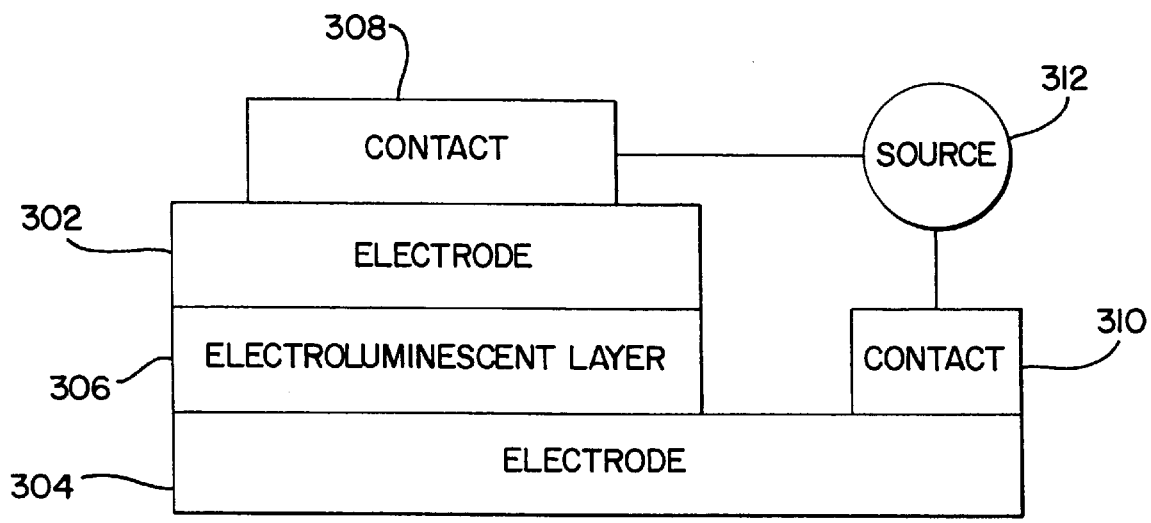
FIG. 3 is a schematic of an electroluminescent device according to a one embodiment of the invention.
Figure 4:
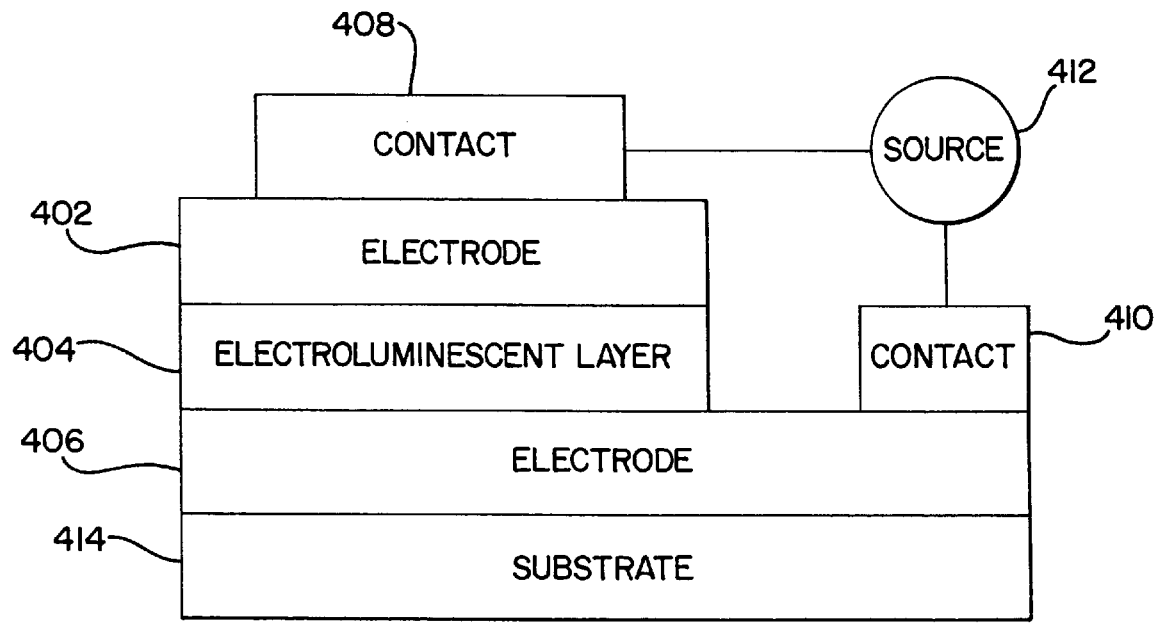
FIG. 4 is a schematic of an electroluminescent device according to a second embodiment of the invention.

The electroluminescent material, such as illustrated at 304 in FIG. 3 and 404 in FIG. 4, comprises, in one embodiment, an organo-siloxane polymer having the basic structure shown below (Compound 1) in which the organic constituents of the organo-siloxane polymer are included in the main chain of the polymer.

Compound 1

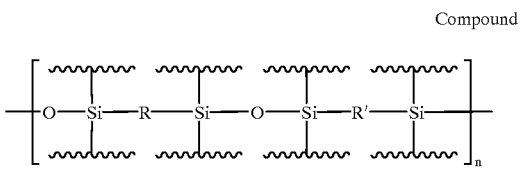

In Compound 1, R and R' can be identical or different as described hereinbelow. In one embodiment, R and R' are selected independently from the group consisting of alkenyl, alkynyl, aralkyl, aryl, heteroaralkyl, and heteroaryl, said organic component being substituted optionally with hydrogen, alkyl, aryl, heteroalkyl, heteroaralkyl, nitro, cyano, hydroxy, alkoxy, aryloxy, thio, alkylthio, arylthio, amino, halogen, dialkylamino, diarylamino, diaralkylamino, arylamino, alkylamino, arylalkylamino, carbonyloxy, carbonylalkoxy, carbonylalkyloxy, alkylcarbonyloxy, arylcarbonyloxy, alkoxylcarbonyloxy, sulfonyl, sulfonyloxy. The organic component (i.e., R or R') includes at least two covalent bonds that couple the organic component to the main chain of the organo-siloxane polymer.

Generally, the organic component of the organo-siloxane polymer of the invention includes any organic compound having useful electroluminescent, hole transport, and/or electron transport properties. Often such organic compounds will include a system of conjugated π-bonds and/or chelated metals. However, the invention is not limited to such compounds. Useful compounds can be determined using methods known to those of skill in the chemical and materials science arts. For example, in some cases computer modeling of the electronic, structural, and packing properties of candidate compounds, alone or combined with measured physical properties, can be used to determine the likely usefulness of the compound. In other cases, the compound, or an analog thereof, can be prepared and its properties determined experimentally.

Examples of useful compounds include poly(phenylene vinylene) compounds, and, more particularly, poly(p-phenylenevinylene) ("PPV", Compound 2). This compound has been found to have useful electroluminescent properties and can be made using methods and materials known in the organic chemical arts (Burroughes, Bradley et al 1990; Burn, Bradley et al. 1992).

Compound 2

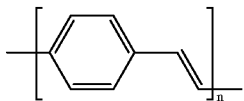

A wide variety of PPV derivatives having useful electroluminescent properties are known and can be used as organic components in the organo-siloxane polymer of the invention. These derivatives include compounds known in the solid-state device arts as MEH-PPV (Braun and Heeger 1991; Braun, Heeger et al. 1991; Braun and Heeger 1992; Parker 1994) and its trimethylsilyl and methoxy derivatives (Zyung, Hwang et al 1995), Cholesterol-PPV (Aratani, Zhang et al. 1993), Diphenyl-PPV (Hsieh, Antoniadis et al. ; Hsieh, Antoniadis et al. 1995), Methoxy-PPV (Zyung, Kim et al. 1995), Nonoxy-PPV (Hamaguchi and Yoshino 1995), Diheptoxy-Dimethoxy-PPV (Yang, Hu et al. 1995), CN-PPV (Greenham, Moratti et al. 1993; Baigent, Hamer et al. 1995; Baigent, Marks et al. 1995; Moratti, Cervini et al. 1995; Staring, Demandt et al. 1995), NBRPV-50 (Baigent, Friend et al. 1995), Dimethyl- and Dimethoxy-PPV(Burn, Bradley et al. 1992), fluorinated PPVs (Benjamin, Faraggi et al. 1996), PPV-anthracene conjugates (Peeters, Delmotte et al. 1997), and dimethyloctylsilyl PPV (Kim, Hwang et al. 1996). Still more useful PPV derivatives include thiophene-PPV conjugates (Baigent, Hamer et al. 1995), "PNV", (Onoda, Ohmori et al. 1995; Tasch, Graupner et al. 1995), the so-called "soluble" PNV (Hanack, Segura et al. 1996), "P(PV-NV)", (Faraggi, Chayet et al 1995), the so-called ladder compounds (Grem, Martin et al. 1995; Grem, Paar et al. 1995; Grimme, Kreyenschmidt et al. 1995; Stampfl, Tasch et al. 1995; Tasch, Niko et aL 1996), pyridyl PPV analogs ("PPyV", (Hessen, Gebler et al.; Marsella, Fu et al. 1995; Tian, Wu et al. 1995, Onoda, 1995 #205)), ethynyl PPV derivatives (Jeglinski, Amir et al. 1995), fluorene-substituted PPV derivatives (Cho, Kim et al. 1997), Ru(bipy)-PPV complexes (Chan, Gong et al. 1997), dimethylsilyl-PPV derivatives (Garten, Hilberer et al. 1997), MEHPPV coupled with anthracene or naphthalene (Barashkov, Novikova et al. 1996), triazole couples with PPV (Grice, Tajbakhsh et al. 1996), and oligophenylenevinylenes ("oligo-PPVs", (Goodson, Li et al. 1997; Maddux, Li et al. 1997)). Still other PPV derivatives are described in U.S. Pat. No. 5,399,502. Additional PPV compounds described in U.S. Pat. No. 5,679,757.

Useful non-PPV organic components include polysilanes (Kido, Nagai et al. 1991; Kido, Nagai et al. 1991; Ebihara, Koshihara et al. 1996; Hattori, Sugano et al. 1996; Suzuki 1996, Fujii, 1996 #126; Suzuki 1996; Suzuki and Hoshino 1996), poly(diphenylquinoxaline) ("PdPhQx", (Yammoto, Inoue et al. 1994)), polyquinoline (Parker 1994; Parker, Pei et al. 1994), polyphenyl-phenylene vinylene ("PPPV", (Dyakonov, Rosler et al. 1995)), polyphenyl ("PPP", (Edwards, Blumstengel et al. 1997)), diphenylacetylenes (Sun, Masuda et al. 1996; Sun, Masuda et al. 1996), poly (ethylene terephthalates and poly(ethylene naphthalates) (Mary, Albertini et al. 1997). Other useful non-PPV organic components include pyrazol-based compounds disclosed in PCT Publication No. WO9828296, aryl amines described in PCT Publication No. WO9830071, poly bi-aryl compounds described in PCT Publication No. WO9836620, organo-beryllium complexes described in PCT Publication No. WO9837736, silacyclopentadiene compounds described in European Patent No. EP0754691, organosilanes described in EP0786924, triamines described in Japanese Patent No. JP09208533, aminoanthracene derivatives described in European Patent No. EP0765106, polyfluorenes described in PCT Publication No. WO9733323, polyheterocycles described in Japanese Patent No. JP09255949, bis (aminophenyl)anthracene derivatives described in Japanese Patent No. JP09268283, phenylenediamines described in Japanese Patent No. JP09268284, triamine derivatives described in European Patent No. EP0805143, compounds described in Japanese Patent Applications Serial Nos. JP10012384, JP10036828, JP10036829, and JP10036830, hydroxyquinolines described in Japanese Patent No. JP10036832, compounds described in European Patent No. EP0825242, arylenevinylene compound described in Japanese Patent No. JP10077467, compounds described in U.S. Pat. Nos. 5,759,444 and 5,759,709, compounds described in European Patent No. EP0847228, arylamine compounds described in Japanese Patent No. 09310066, compounds described in U.S. Pat. No. 5,672,678, compounds described in PCT Publication No. WO9804610, poly (phenylenevinylene) compounds described in U.S. Pat. No. 5,747,182, compounds described in PCT Publication No. WO9813408, triazole derivatives described in U.S. Pat. Nos. 5,792,567 and 5,792,568, distilbene compounds described in Japanese Patent No. JP09003014, JP09020886, and JP09035870, benzotiazole derivatives described in Japanese Patent No. JP09050887, perylene derivatives described in PCT Publication No. WO9828767, poly(arylene ethanediyl) polymers described in U.S. Pat. No. 5,425,125, arylene vinylene polymers described in European Patent No. EP0704094, compounds described in Japanese Patent No. JP10072579, pyrazinoquinoxaline derivatives described in Japanese Patent No. JP09003342, compounds described in Japanese Patent No. JP09003446 and JP09003447, tetraaza-porphyrin compounds described in Japanese Patent No. JP09013024, quinoxaline compounds described in Japanese Patent No. JP09013025 and JP09013026, quinacridone compounds described in U.S. Pat. No. 5,593,788, compounds described in Japanese Patent No. JP09031454 and JP09031455, compounds described in Japanese Patent No. JP09045478, cournarin derivatives described in Japanese Patent No. JP09053068, iminostilbene compounds described in Japanese Patent No. 090592565, compounds described in European Patent No. EP0761772, compounds described in Japanese Patent No. JP09087616, arylamine compounds described in European Patent No. EP0731625, amine compounds described in Japanese Patent No.

JP09095470, metallo-organic complexes described in Japanese Patent No. JP09111234, compounds described in Japanese Patent No. JP09111233, hydrazone compounds described in U.S. Pat. No. 5,629,421, benzoxazinones described in European Patent No. EP0775179, naphthalimide compounds described in European Patent No. EP0775180, compounds described in European Patent No. EP0743809, amine compounds described in Japanese Patent No. JP09143130, compounds described in Japanese Patent No. JP09148072, aminoanathracene compounds described in Japanese Patent No. JP09157643, organo-metallic complexes described in Japanese Patent No. JP09165390, JP09165391, JP09227576, and, JP09175529, compounds described in Japanese Patent No. JP09165573, compounds described in European Patent No. EP0766498, organo-metallic complexes described in Japanese Patent No. JP09194831, hydrazone derivatives described in Japanese Patent No. JP09202762, acenaphthene derivatives described in Japanese Patent No. JP09216855, polycyclic ring systems described in Japanese Patent No. JP09241629, oxadiazolinated polymers described in Japanese Patent No. JP09255725, organosilane compounds described in Japanese Patent No. JP09263754, compounds described in Japanese Patent No. 09255949, JP09268383, JP09268284, chelating compounds described in Japanese Patent No. JP09279136, compounds described in Japanese Patent No. JP09286980 and JP09291274, compounds described in European Patent No. EP0805143, porphyrin derivatives described in Japanese Patent No. JP09296166, compounds described in Japanese Patent No. JP09302337, compounds described in Japanese Patent No. JP09316440, silane derivatives described in PCT Publication No. WO9746605, compounds described in Japanese Patent No. JP09324176, quinoline derivatives described in Japanese Patent No. JP09328472, organometallic complexes described in Japanese Patent Applications Serial Nos. JP09328678 and JP09328679, oxadiazole derivatives described in U.S. Pat. No. 5,702,833, organo-aluminum complexes described in Japanese Patent No. JP10025472, compounds described in Japanese Patent No. JP10045722, arylenevinylene compounds described in Japanese Patent No. JP10046138, compounds described in Japanese Patent No. JP10053759, benzazole derivatives described in European Patent No. EP0825804, compounds described in Japanese Patent Nos. JP100072580 and JP100072581, triamine compounds described in Japanese Patent No. JP10077252, silane compounds described in Japanese Patent No. JP10081874, compound described in U.S. Pat. No. 5,755,999, compounds described in U.S. Pat. No. 5,766,515, and benzazole compounds described in U.S. Pat. No. 5,766,779.

In a more particular embodiment, the organic component is selected from the group consisting of alkylene, aralkylene, arylene, heteroaralkylene, and heteroarylene. In a more specific embodiment, the organic component is arylene or heteroarylene. In a still more specific embodiment, the organic component is arylene. More particular arylenes useful in the invention are those comprising a polycyclic aromatic hydrocarbon containing between 2 and 7 fused aromatic rings. Still more particular embodiments, R and R' are arylenes containing between 2 and 7 fused aromatic rings selected from the group consisting of electroluminescent agents, hole transport agents, electron transport agents, and combinations thereof. In other words, R and R' independently can be an electroluminescent agent, a hole transport agent, an electron transport agent, or a combination of such agents. Thus, it will be appreciated by those of skill in the organic chemical and materials science arts that an organo-siloxane polymer of the invention can comprise an electroluminescent agent, a hole transport agent, an electron transport agent, or a combination of such agents in the main chain of the polymer.

The organic component can be coupled with the main chain of the organo-siloxane polymer of the invention using methods and materials known to those of skill in the organic chemical arts. For example, organic component precursors including trihalosilyl-, trialkoxysilyl-, dihaloalkylsilyl-, dialkoxyalkylsilyl-, dialkylhalosilyl-, or dialkylalkoxysilyl-functionalities can be used to couple the organic component with the main chain of the organo-siloxane polymer. One method for attachment of such functionalities is through hydrosilation. Hydrosilation has been successfully accomplished under a wide variety of conditions using a wide range of reagents, catalysts and substrates (Ojima 1989; Hiyama and Kusumoto 1991; 1992).

In one embodiment, the organic component is an electroluminescent agent. More particularly, in one embodiment, R and R' independently are anthracene and pentacene. In a more specific embodiment, the organic component is anthracene. The anthracene component of the organo-siloxane polymer each can be substituted optionally as described above with respect to Compound 1. In one embodiment of Compound 1, the main-chain siloxane polymer includes the anthracene derivative shown as Compound 3 below.

Compound 3

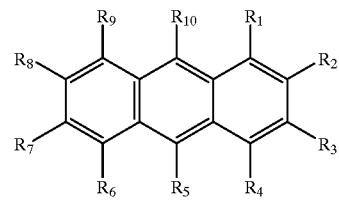

$R_1$–$R_{10}$ are selected independently from the group of substituents recited above with respect to R and R' of Compound 1. In one particular embodiment, two substituents are coupled with the adjacent silicon atoms of the main chain. In a more particular embodiment, these two substituents are located symmetrically on the anthracene molecule (e.g., $R_1$ and $R_4$, $R_2$ and $R_7$, or $R_5$ and $R_{10}$). In a more particular embodiment, at least one of the substituents is an alkylene group. In a still more particular embodiment, the alkylene group has the general formula —$CH_2(CH_2)_m CH_2$—, where m is an integer between 0 and 4. Still more particularly, m is 1, i.e., the substituent is trimetiylene: —$CH_2CH_2CH_2$—.

In yet another particular embodiment, the silicon-coupled substituents are identical. More particular embodiments are those for which the two substituents are $R_5$ and $R_{10}$, where $R_5$=$R_{10}$ and $R_1$–$R_4$ and $R_6$–$R_9$ are chosen from the group listed above with respect to Compound 3. Still more particular embodiments are those embodiments just recited for which $R_5$ and $R_{10}$ are the same alkylene moiety. Yet more particular embodiments are those for which the alkylene moiety is of the general formula —$CH_2(CH_2)_m CH_2$—, and, more particularly, where m is an integer between 0 and 4. One particular embodiment having useful electroluminescent properties is that embodiment for which $R_5$ and $R_{10}$ each are —$CH_2CH_2CH_2$—, and $R_1$–$R_4$ and $R_6$–$R_9$ each are hydrogen. This compound has the structure shown below (Compound 4).

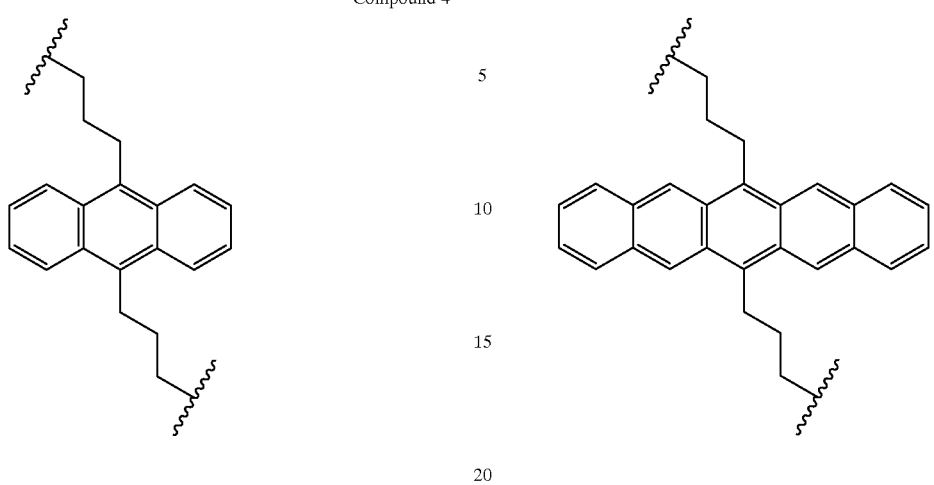

Compound 4

Compound 6

In another embodiment of Compound 1, the main-chain siloxane polymer includes pentacene. The pentacene component of the organo-siloxane polymer has the general formula shown as Compound 5 below.

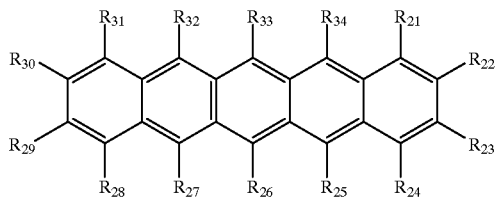

Compound 5

$R_{21}$–$R_{34}$ are selected independently from the group consisting of substitutents described above with respect to Compound 1. In one particular embodiment, two substituents are coupled with the adjacent silicon atoms of the main chain. In a more particular embodiment, these two substituents are located symmetrically on the pentacene molecule (e.g., $R_{22}$ and $R_{29}$ or $R_{26}$ and $R_{33}$). In a more particular embodiment, at least one of the substituents is an alkylene group. In a still more particular embodiment, the alkylene group has the general formula —$CH_2(CH_2)_m CH_2$—, where m is an integer between 0 and 4. Still more particularly, m is 1, i.e., the substituent is trimethylene: —$CH_2CH_2CH_2$—.

In yet another particular embodiment, the silicon-coupled substituents are identical. More particular embodiments are those for which the two substituents are $R_{26}$ and $R_{33}$, where $R_{26}$=$R_{33}$ and $R_{34}$–$R_{25}$ and $R_{27}$–$R_{32}$ are chosen from the group listed above with respect to Compound 5. Still more particular embodiments are those embodiments just recited for which $R_{26}$ and $R_{33}$ are the same alkylene moiety. Yet more particular embodiments are those for which the alkylene moiety is of the general formula —$CH_2(CH_2)_m CH_2$—, and, more particularly, where m is an integer between 0 and 4. One particular embodiment having useful electroluminescent properties is that embodiment for which $R_{26}$ and $R_{33}$ each are —$CH_2CH_2CH_2$—, and $R_{34}$–$R_{25}$ and $R_{27}$–$R_{32}$ each are hydrogen. This compound has the structure shown below (Compound 6).

The above-described compounds can be made using methods known among those of skill in the art of organic chemistry and materials science arts. In general, the substituents for both Compound 3 and Compound 5 will be chosen to provide desired electronic and mechanical properties. The choice of substituent or combination of substitutents will depend at least in part upon the emission color, electrical, and optical properties required of the intended device. Such choices can be made by considering various well-known chemical properties including, but not limited to, steric factors, electron-withdrawing effects, electron-donating effects, and resonance effects. Often such properties can be estimated, e.g., using chemical modeling software or published parameters. Many such properties can be determined empirically using standard methods and materials.

For example, the organo-siloxane polymer described above (Compound 1) can be formed from anthracene or pentacene optionally substituted as just described and including at least one reactive silyl group that is effective to form siloxane bonds. Examples of such reactive silyl groups include trialkoxysilyl, dialkoxysilyl, trichlorosilyl, dichlorosilyl, heptachlorotrisiloxy, and pentachlorodisiloxy. In more particular embodiments, the present invention provides the following precursors (Compound 7 and Compound 8).

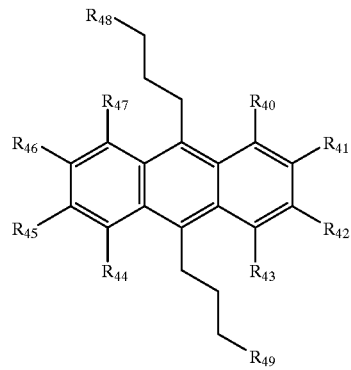

Compound 7

Compound 8

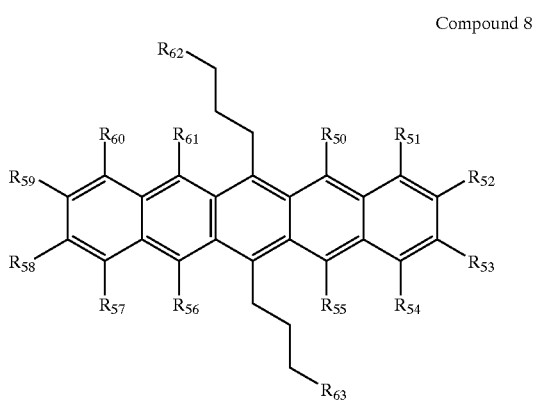

$R_{40}$–$R_{43}$ and $R_{44}$–$R_{47}$, and $R_{50}$–$R_{55}$ and $R_{56}$–$R_{61}$ are selected independently from the group of substituents described above with respect to Compound 1. $R_{48}$, $R_{49}$, $R_{62}$, and $R_{63}$ are selected independently from the group consisting of trialkoxysilyl, dialkoxysilyl, trichlorosilyl, dichlorosilyl, heptachlorotrisiloxy, and pentachlorodisiloxy. In one embodiment, $R_{40}$–$R_{47}$ and $R_{50}$–$R_{61}$ are as just described, and $R_{48}$, $R_{49}$, $R_{62}$, and $R_{63}$ each are trichlorosilyl. In a more specific embodiment, $R_{40}$–$R_{47}$ and $R_{50}$–$R_{61}$ are each hydrogen and $R_{48}$, $R_{49}$, $R_{62}$, and $R_{63}$ each are trichlorosilyl.

For example, the synthesis of Compound 4 from 9,10-bis (3-trichlorosilylpropyl)anthracene (Compound 7 where $R_{40}$–$R_{47}$ and $R_{50}$–$R_{61}$ are each hydrogen, and $R_{48}$, and $R_{49}$ each are trichlorosilyl) is described in Section 6.1. The general synthetic route is outlined in FIG. 1 below.

Figure 1

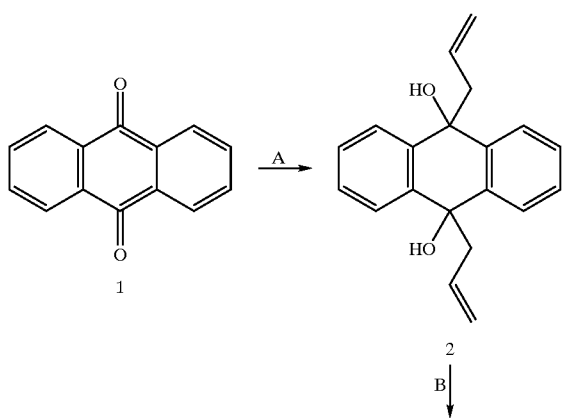

In step A, commercially available anthraquinone 1 (Aldrich Chemical Co., Madison Wis.) is reacted with allyl magnesium bromide ($CH_2CHCH_2MgBr$, also available commercially from Aldrich) in dry ether to form addition product 2. Product 2 is dehydrated using phenylhydrazine and acetic acid (B). The resulting bis-allylanthracene 3 is reacted with trichlorosilane ($HSiCl_3$) and $H_2PtCl_6 \cdot H_2O$ in dry benzene (C) to give the desired final hydrosilation product 4. The pentacene analog can be made using the same synthetic pathway. In general, product 4—the anti-Markovnikov product—is the dominant species. However, it will be appreciated by those of skill in the organic chemistry arts that other alkenes will likely give both Markovnikov as well as anti-Markovnikov hydrosilation products. Nevertheless, both the Markovnikov and anti-Markovnikov addition products can be incorporated into the organo-siloxane polymers of the invention, either in combination or individually after isolation using known methods and materials.

In still other embodiments, the main-chain silicon atoms or the organo-siloxane polymer having the general structure shown above as Compound 1 are cross-linked with the silicon atoms of other such organo-siloxane polymer chains to form two- and three-dimensional organo-siloxane networks. In more particular embodiments, the cross-links are made by oxygens atom to provide siloxane cross-links. Other cross-links can be formed using atoms or molecules that impart desired mechanical and electronic properties to the matrix, such as, for example, methylene (—$CH_2$—), silicon (—Si—), or oxyalkyleneoxy (e.g. oxymethyleneoxy: —O—$CH_2$—O—). Still other cross-linking agents will be familiar to those of skill in the organic chemical and materials science arts.

The electroluminescent material can further be doped with a hole transport material, an electron transport material, an organic or inorganic dye, or a combination of such materials/dyes to alter the color and enhance the light emitting quality of the luminescent organic-inorganic hybrid material. Generally, many compounds that act as electroluminescent agents can also function as electron transport or hole transport agents as well. Generally, electroluminescent agents can be identified by their fluorescence properties, hole transport agents by large electron densities (i.e., "electron rich" compounds), and electron transport agents by low electron densities (i.e., "electron deficient" compounds). In addition, a useful electroluminescent, hole transport, or electron transport agent will be electrochemically and structurally robust as determined, for example, by the ability of the compound to withstand repeated redox cycles. Examples of suitable hole transport agents include, but are not limited to, porphyrins or aromatic tertiary amines, in addition to the compounds described in PCT Publication No. WO9801011, the quinacridone derivatives described in U.S. Pat. No. 5,725,651, the compounds described in Japanese Patents Nos. JP09298089, JP09249621, and JP09194441. Examples of suitable electron transport agents include, but are not limited to, oxadiazole derivatives such as described in U.S. Pat. No. 5,276,381, which is incorporated reference above, or thiadiazole derivatives, such as disclosed in U.S. Pat. No. 5,336,546, also incorporated by reference above. Still other electron transport agents include the compounds described in Japanese Patents Nos. JP09003448 and JP09139288. Examples of suitable dyes include perylene, coumarin, and rhodamine or a rhodamine salt such as rhodamine perchlorate, as well as the quinacridone derivatives described in U.S. Pat. No. 5,725,651. Again, the choice of materials and their preparation can be accomplished using techniques well known in the organic chemical and materials science arts. Also, as noted above, the hole transport, electron transport, and dye compounds can be included in the main chain of the organo-siloxane polymer of the invention.

The electroluminescent layer can be formed by standard methods including, but not limited to, physical vapor deposition methods, sputtering, spin-coating, or solution casting. The layer may be formed directly on the first electrode (see Sections 6.3.1 and 6.3.2). In addition, the layer can be doped with a hole transport material, an electron transport material, an organic dye, and/or a combination of the above to enhance its performance (see Section 6.3.3). In some embodiments, all of the components of the electroluminescent material (i.e., the electroluminescent agent and any hole transport, electron transport agent) are provided in a single organo-siloxane polymer. In another embodiment, one or more of the components of the electroluminescent material is provided in a separate organo-siloxane polymer and the polymers provided either in a single deposition (i.e., as a mixture) or in separate depositions (i.e., as two or more layers). The different depositions can be provided without significant chemical coupling thus providing distinct strata of materials, or the deposited materials can be chemically linked to form cross-links between the polymers of the depositions. Combinations of cross-linked and non-cross-linked deposition layers can be used as well. For example, two layers can be cross-linked and a third layer not cross-linked. In still other embodiments, the electroluminescent agent is provided in an organo-siloxane polymer as described herein, and one or more dopants selected from the group consisting of hole transport agents, electron transport agents, and dyes is added.

A wide range of polymer stoichiometries and composition ratios can be used to form the electroluminescent materials of the present invention. The determination of such stoichiometries and composition ratios can be determined using methods and materials known to those of skill in the materials science arts and will generally depend at least in part on the compounds being tested, the colors and intensities desired, and the mechanical properties of the resulting electroluminescent material. In some cases, the organic component of the electroluminescent material will include only an electroluminescent agent and, optionally, one or more dopants (including dyes, hole transport agents, electron transport agents, and other electroluminescent agents). In other cases a hole transport and/or electron transport agent will be included in the main chain of the organo-siloxane polymer along with the electroluminescent agent. Again, a dopant (e.g., a dye) can be included as well. Also, the present invention further includes organo-siloxane polymers in which the main chain includes hole and electron transport agents. A dopant including other hole and/or electron transport agents, electroluminescent agents and dyes can also be included. As noted above, a plurality of polymers having one or more of the formulations just described can be combined in one or more layers which can be cross-linked or kept chemically uncoupled as desired.

Generally, following deposition, the material is reacted in a humid atmosphere or open air to cure the electroluminescent layer under conditions allowing thermodynamic control of product formation. In one embodiment, the material is exposed to about 100% humidity for about 5 minutes to about 10 minutes and is heated at about 110° C. for about 15 minutes. In another embodiment, the material is exposed to ambient atmospheric moisture prior to heating at 110° C. for about 15 minutes. Still other combinations of reaction conditions will be apparent to those of skill in the organic chemical and materials science arts.

Without wishing to be bound to any particular theory of action, it is believed the chemical reaction of the above-mentioned reactive silyl groups of the organic component of the organo-siloxane polymer (e.g., the above-described trichlorosilyl or trialkoxysilyl groups) with moisture creates an interlocking organic-inorganic hybrid polymeric material comprising silicon-oxygen bonds (e.g., —Si—O—Si—). Generally, water displaces the chloride or alkoxide group to form a hydroxysilane. The hydroxysilane moiety reacts again to displace another chlorine-silicon or alkoxy-silicon bond to form the siloxane network. This reaction sequence is illustrated in FIG. 5A, in which a bis(trichlorosilyl) organic component 502 reacts with water in a first step to form an hydroxysilyl derivative 504. The intermediate reacts with additional trichlorosilyl starting material in a second step to form an organo-siloxane polymer intermediate 506. Thus, those of skill in the organic chemistry arts will recognize the Si—Cl bonds of the starting material 502 do not undergo condensation. Further reaction and cross-linking provides organo-siloxane polymer network 508. Alternatively, as illustrated in FIG. 5B, starting material 502 can be reacted with a hydroxylated surface 510 to form, upon reaction with additional starting material, a substrate-bound organo-siloxane polymer network 512.

6 EXAMPLES

The following Examples are provided to illustrate certain aspects of the present invention and to aid those of skill in the art in practicing the invention. These Examples are in no way to be considered to limit the scope of the invention in any manner.

6.1 Synthesis of Light-Emitting Layer Precursors
6.1.1 9,10-Diallylanthracene A solution of allylmagnesium bromide was prepared by adding dropwise with vigorous stirring 40 ml of allyl bromide (Aldrich) dissolved in 100 ml of diethyl ether to a mixture of 50 g of magnesium turnings in 300 ml of anhydrous ether. The mixture was stirred for 2 hours following the addition, and the ethereal solution was then transferred to a reaction flask. This flask and transferred solution was cooled to 0° C., and 20 g of anthraquinone (Aldrich) was added in 500 mg portions.

The anthraquinone/allyl magnesium bromide solution was stirred for 14 h and then warmed slowly to room temperature. The temperature of the reaction mixture was reduced to 0° C., and then ice was added to the mixture until a yellow ether solution was formed. This solution was separated from the rest of the reaction mixture and reduced in vacuo until a white precipitate formed. The precipitate was washed with petroleum ether and dried in vacuo. The solid was mixed with 6 ml of phenylhydrazine and 26 ml of glacial acetic acid and then was heated at 40° C. for 2 hours, refluxed for 30 minutes, and then cooled to room temperature over a period of 12 hours. A yellow powder precipitated from the reaction mixture. The powder was recrystallized from acetic acid and ethanol. Characterization: Elemental Analysis (Theory (Found)): C:93.02 (92.75), H: 6.98 (7.10).

6.1.2 9,10-Bis(trichlorosilylpropyl)anthracene 1 g of 9,10-Diallylanthracene (prepared as described in Section 6.1.1 above) was dissolved in 20 ml of dry toluene. A single crystal of hydrogen hexachloroplatinum was added to the solution, followed by 1 ml of trichlorosilane. The mixture was stirred at 40° C. for 9 hours after which time the volatile components were removed in vacuo. The remaining solid was sublimed, yielding a yellow solid having the following mass spectrographic characteristic: MS (M+): 578. $^1$H NMR (200 MHz, $C_6D_6$): 8.12 (dd, 4 H, J=10.4 Hz); 7.34 (dd, 4 H, J=10.1 Hz); 3.34 (t, 4 H, J≈8.14 Hz); 1.85 (tt, 4 H, J=8.14 Hz); 1.09 (t, 4 H, 8.3 Hz).

6.2 Preparation of the Device Substrate

A sheet of indium-tin oxide-coated glass (7"×7", Donnally) was cut into 1"×1" squares. Each of the squares was sonicated for 10 minutes in successive baths of acetone, methanol, and reverse osmosis de-ionized water. The squares were then dried at 110° C. for 12 hours prior to use.

6.3 Device Construction 6.3.1 Devices of Structure 1

A surface layer of 9,10-bis(trichlorosilylpropyl) anthracene having a thickness of about 100 nm was deposited onto a clean ITO substrate (see Section 6.2) by resistive heating at a rate of about 0.2 mn/sec at a pressure of about $10^{-6}$ Torr. The anthracene layer was then exposed to ambient atmosphere for about 15 minutes and then heated to 110° C. for about 30 minutes. A 300 nm layer of magnesium metal (Cerac) was deposited over the bis(trichlorosilylpropyl) anthracene layer by resistive heating at a rate of about 0.5 nm/sec at a pressure of about $10^{-6}$ Torr. A pale violet emission having an approximate intensity of 100 cd/m$^2$ emanated from the device upon application of 12 V of direct current (DC).

6.3.2 Devices of Structure 2

An anhydrous solution of 9,10-bis(trichlorosilylpropyl) anthracene in xylene (1% by weight) was spun-cast onto a clean ITO substrate (prepared as described in Section 6.2) at 2,000 revolutions-per-minute ("rpm") for 60 seconds ("s"). The coated substrate was placed in a humidity chamber having an ambient humidity of 100% and a temperature of 25° C. for 15 minutes ("min"). The device was then heated to 110° C. for about 0.5 hours ("hrs.") A layer of magnesium metal (Cerac) was deposited by resistive heating over the bis(trichlorosilylpropyl)anthracene layer to a thickness of about 300 nm at a rate of about 0.5 nm/s and a pressure of about $10^{-6}$ Torr. A pale violet emission having an intensity of about 100 cd/m$^2$ was observed upon the application of a 12 V DC current to the device.

6.3.3 Devices of Structure 3

An anhydrous solution of 9,10-bis(trichlorosilylpropyl) anthracene in xylene (1% by weight) and tetraphenylporphyrin (0.1% by weight) was spun-cast onto a clean ITO substrate (prepared as described in Section 6.2) at 4,000 rpm for 30 s. The coated substrate was placed in a humidity chamber having an ambient humidity of 100% and a temperature of 25° C. for 15 min. The device was then heated to 110° C. for about 0.5 hrs. A layer of magnesium metal (Cerac) was deposited by resistive heating over the bis (trichlorosilylpropyl)anthracene/tetraphenylporphyrin layer to a thickness of about 300 nm at a rate of about 0.5 nm/s and a pressure of about $10^{-6}$ Torr. A pale violet emission having an intensity of about 100 cd/m$^2$ was observed upon the application of a 8 V DC current to the device.

6.3.4 Devices of Structure 4

An anhydrous solution of 9,10-bis(trichlorosilylpropyl) anthracene in xylene (1% by weight) and coumarin 6 (1% by weight) was spun-cast onto a clean ITO substrate (prepared as described in Section 6.2) at 4,000 rpm for 30 s. The coated substrate was placed in a humidity chamber having an ambient humidity of 100% and a temperature of 25° C. for 5 min. The device was then heated to 110° C. for about 1 hour. A layer of magnesium metal (Cerac) was deposited by resistive heating over the bis(trichlorosilylpropyl) anthracene/coumarin 6 layer to a thickness of about 150 nm at a rate of about 2 m/s and a pressure of about $10^{-6}$ Torr. A green emission having an intensity of about 100 cd/m$^2$ was observed upon the application of a 5 V DC current to the device.

6.3.5 Devices of Structure 5

An anhydrous solution of 9,10-bis(trichlorosilylpropyl) anthracene in tetrahydrofuran (1% by weight) and rhodamine perchlorate (1% by weight) was spun-cast onto a clean ITO substrate (prepared as described in Section 6.2) at 4,000 rpm for 30 s. The coated substrate was placed in a humidity chamber having an ambient humidity of 100% and a temperature of 25° C. for 5 min. The device was then heated to 110° C. for about 1 hour. A layer of magnesium metal (Cerac) was deposited by resistive heating over the bis(trichlorosilylpropyl)anthracene/rhodamine layer to a thickness of about 150 nm at a rate of about 2 nm/s and a pressure of about $10^{-6}$ Torr. A red emission having an intensity of about 30 cd/m$^2$ was observed upon the application of a 5 V DC current to the device.

6.3.6 Devices of Structure 6

An anhydrous solution of 9,10-bis(trichlorosilylpropyl) anthracene in xylene (1% by weight) and perylene (1% by weight) was spun-cast onto a clean ITO substrate prepared as described in Section 6.2) at 4,000 rpm for 30 s. The coated substrate was placed in a humidity chamber having an ambient humidity of 100% and a temperature of 25° C. for 5 min. The device was then heated to 110° C. for about 1 hour. A layer of magnesium metal (Cerac) was deposited by resistive heating over the bis(trichlorosilylpropyl) anthracene/perylene layer to a thickness of about 150 nm at a rate of about 2 nm/s and a pressure of about $10^{-6}$ Torr. A green emission having an intensity of about 30 cd/m$^2$ was observed upon the application of a 5 V DC current to the device.

7 Conclusion

Thus, the present invention will be seen to provide a light-weight, durable, efficient electroluminescent device. Such devices can be used in a wide variety of applications in consumer and military electronics, such as computers and visual display terminals.

Although certain embodiments and examples have been used to describe the present invention, it will be apparent to those having skill in the art that various changes can be made to those embodiment and/or examples without departing from the scope or spirit of the present invention. For example, other substituents having similar electronic and steric properties can be used in addition to those exemplified herein without departing from the scope of the invention. A wide variety of processing techniques can be used to provide the cross-linked siloxane network provided by the present invention.

8 Bibliography

The following materials are incorporated herein by reference in their entirety and for all purposes.

1. (1992). *Comprehensive Handbook on Hydrosilation.* Oxford, Pergammon Press.
2. Aratani, S., C. Zhang, et al. (1993). "Improved Efficiency in Polymer Light-Emitting Diodes Using Air-Stable Electrodes." *J. Elect. Mat.* 22: 745.
3. Baigent, D. R., R. H. Friend, et al. (1995). "Blue Electroluminescence from a Novel Polymer Structure." *Syn. Met.* 71: 2171.
4. Baigent, D. R., P. J. Hamer, et al. (1995). "Polymer Electroluminescence in the Near Infra-M Red." *Syn. Met.* 71: 2175.
5. Baigent, D. R., R. N. Marks, et al. (1995). "Surface-Emitting Polymer Light-Emitting Diodes." *Syn. Met.* 71(2177).
6. Barashkov, N. N., T. S. Novikova, et al. (1996). "Synthesis and Spectral Properties of Poly(Arylenevinylenes) Incorporating 2-Methoxy-5-(2'-Ethylhexyloxy)-p-Phenylene Fragments in the Polymer Chain." *Syn. Met.* 83: 39.
7. Benjamin, I., E. Z. Faraggi, et al. (1996). "Fluorinated Poly(p-Phenylenevinylene) Copolymers: Preparation and Use in Light-Emitting Diodes." *Chem. Mat.* 8: 352.
8. Braun, D. and A. J. Heeger (1991). "Visible Light Emission from Semiconducting Polymer Diodes." *Appl. Phys. Lett.* 58: 1982.
9. Braun, D. and A. J. Heeger (1992). "Electroluminescence from Light-Emitting Diodes Fabricated from Conducting Polymers." *Thin Solid Films* 216: 96.
10. Braun, D., A. J. Heeger, et al. (1991). "Improved Efficiency in Semiconducting Polymer Light-Emitting Diodes." *J. Elect. Mat.* 20: 945.
11. Burn, P. L., D. D. C. Bradley, et al. (1992). "Precursor Route Chemistry and Electronic Properties of Poly(p-Phenylenevinylene). (Poly[(2,5-Dimethoxy-p-Phenylene) Vinylene]." *J. Chem. Soc.* Perkin Trans. 1: 3225.
12. Burroughes, J. H., D. D. C. Bradley, et al (1990). "Light-Emitting Diodes Based on Conjugated Polymers." *Nature* 347: 539.
13. Chan, W. K., X. Gong, et al. (1997). "Photoconductivity and Charge Transporting Properties of Metal-Containing Poly(p-Phenylenevinylene)s." *AppL. Phys. Lett.* 71: 2919.
14. Cho, H. N., D. Y. Kim, et al. (1997). "Blue and Green Light Emission from New Soluble Alternating Copolymers." *Adv. Mater* 9: 236.
15. Dyakonov, V., G. Rösler, et al. (1995). "Magnetic Resonance in Films and Photodiodes Based on Poly-(phenyl-phenylene-vinylene)." *J. AppL. Phys.* 79: 1556–1562.
16. Ebihara, K., S. Koshihara, et al. (1996). "Polysilane-Based Polymer Diodes Emitting Ultraviolet Light." *Jpn. J. AppL. Phys.* 35: L1278–L1280.
17. Edwards, A., S. Blumstengel, et aL (1997). "Blue Photo- and Electroluminescence from Poly(benzoyl-1,4-phenylene)." *App. Phys. Lett.* 70(3): 298–300.
18. Faraggi, E. Z., H. Chayet, et al. (1995). "Tunable Electroluminescence and Photoluminescence in Phenylenevinylene-Naphthylene-vinylene Copolymers**." *Adv. Mat.* 7: 742.
19. Garten, F., A. Hilberer, et al. (1997). "Efficient Blue LEDs from a Partially Conjugated Si-Containing PPV Copolymer in a Double-Layer Configuration." *Adv. Mater* 9: 127.
20. Goodson, T., W. Li, et al. (1997). "Oligophenylenevinylenes for Light Emitting Diodes." *Adv. Mater.* 9: 639–643.
21. Greenham, N. C., S. C. Moratti, et al. (1993). "Efficient Light-Emitting Diodes Based on Polymers with High Electron Affinities." *Nature* 365: 628.
22. Grem, G., V. Martin, et al. (1995). "Stable Poly(Para-Phenylene)s and their Application in Organic Light Emitting Devices." *Syn. Met.* 71: 2193.
23. Grem, G., C. Paar, et al. (1995). "Soluble Segmented Stepladder Poly(p-Phenylenes) for Blue-Light-Emitting Diodes." *Chem. Mat.* 7: 2.
24. Grice, A. W., A. Tajbakhsh, et al. (1996). "A Blue-Emitting Triazole-Based Conjugated Polymer." *Adv. Mater* 9: 1174.
25. Grimme, J., M. Kreyenschmidt, et al. (1995). "On the Conjugation Length in Poly(para-Phenylene)-Type Polymers." *Adv. Mat.* 7: 292.
26. Harnaguchi, M. and K. Yoshino (1995). "Polarized Electroluminescence from Rubbing-Aligned Poly(2,5-Dinonyloxy-1,4-Phenylenevinylene) Films." *Appl. Phys. Lett* 67: 3381.
27. Hanack, M., J. L. Segura, et al. (1996). "New LEDs Based on Soluble Poly(2,6-Naphthylenevinylene)." *Adv. Mater* 8: 663.
28. Hattori, R., T. Sugano, et al. (1996). "Room Temperature Ultraviolet Electroluminescence from Evaporated Poly (dimethylsilane) Film." *Jpn. J. Appl. Phys.* 35: L1509–L1511.
29. Hessen, S. W., D. D. Gebler, et al. "Photophysics of Poly(p-Pyridine): Blue Electroluminescent Devices from a Soluble Conjugated Polymer." *Polymer Preprints* XXXX.
30. Hiyama, T. and T. Kusumoto (1991). Comprehensive Organic Synthesis. Trost, B. M New York, Pergammon Press. 3: 763.
31. Hsieh, B. R., H. Antoniadis, et al. "A Chlorine Precursor Route (CPR) to Poly(p-Phenylene Vinylene) Light Emitting Diodes." *Polymer Preprints* XXXX 465.
32. Hsieh, B. R., H. Antoniadis, et al. (1995). "Chlorine Precursor Route (CPR) Chemistry to Poly(p-phenylene vinylene)-Based Light Emitting Diodes." *Adv. Mat.* 7(1): 36.
33. Jeglinski, S. A., O. Amir, et al. (1995). "Symmetric Light Emitting Devices from Poly(p-di Ethynylene Phenylene) (p-di Phenylene Vinylene) Derivatives." *Appl. Phys. Lett.* 67: 3960.
34. Kido, J., K. Nagai, et al. (1991). "Electroluminescence from Polysilane Film Doped with Europium Complex." *Chemistry Letters*: 1267–1270.
35. Kido, J., K. Nagai, et al. (1991). "Poly (methylphenylsilane) Film as a Hole Transport Layer in Electroluminescent Devices." *AppL. Phys. Lett.* 59(21): 2760–2762.
36. Kim, S. T., D. H. Hwang, et aL (1996). "Efficient Green Electroluminescent Diodes Based on Poly(2-Dimethyloctylsilyl-1,4-Phenylenevinylene)." *Adv. Mater* 8: 979.
37. Maddux, T., W. Li, et al. (1997). "Stepwise Synthesis of Substituted Oligo(phenylenevinylene) via an Orthogonal Approach." *J. Am. Chem. Soc.* 119: 844–845.
38. Marsella, M. J., D. K. Fu, et al. (1995). "Synthesis of Regioregular Poly(Methyl Pyridinium Vinylene): An Isoelectronic Analogue to Poly(Phenylene Vinylene)." *Adv. Mat.* 7: 145.
39. Mary, D., M. Albertini, et al. (1997). "Understanding Optical Emissions from Electrically Stressed Insulating Polymers: Electroluminescence in Poly(ethylene terephthalate) and Poly(ethylene 2,6-naphthalate) Films." *J. Phys. D: Appl. Phys.* 30: 171–184.
40. Moratti, S. C., R. Cervini, et al. (1995). "High Electron Affinity Polymers for LEDs." *Syn. Met.* 71: 2117.
41. Ojima, I. (1989). The Chemistry of Orgnaic Silicon Compounds. S. Patai and Z. Rappoport. Chichester, Wiley: 1479.

42. Onoda, M., Y. Ohmori, et al. (1995). "Visible-Light Electroluminescent Diodes Using Poly(arylene Vinylene)." *Syn. Met.* 71: 2181.
43. Parker, I. D. (1994). "Carrier Tunneling and Device Characteristics in Polymer Light-Emitting Diodes." *J. Appl. Phys.* 75: 1656.
44. Parker, I. D., Q. Pei, et aL (1994). "Efficient Blue Electroluminescence from a Fluorenated Polyquinoline." *App. Phys. Lett.* 65(10): 1272–1274.
45. Peeters, E., A. Delmotte, et al. (1997). "Chiroptical Properties of Poly{2,5-bis[(S)-2-Methylbutoxy]-1,4-Phenylene Vinylene}." *Adv. Mater* 9: 493.
46. Starnpfl, J., S. Tasch, et al. (1995). "Quantum Efficiencies of Electroluminescent Poly(Para-Phenylenes)." *Syn. Met.* 71: 2125.
47. Staring, E. G. J., R. C. J. E. Demandt, et al. (1995). *Syn. Met.* 71: 2179.
48. Sun, R., T. Masuda, et al. (1996). "Blue Electroluminescence from Substituted Polyacetylenes." *Jpn. J. Appl Phys.* 35: L1673–L1676.
49. Sun, R., T. Masuda, et al. (1996). "Green Electroluminescence from Substituted Polyacetylenes." *Jpn. J. Appl. Phys.* 35: L1434–L1437.
50. Suzuki, H. (1996). *Appl. Phys. Lett.* 69.
51. Suzuki, H. (1996). "Fabrication of Electron Injecting Mg:Ag Alloy Electrodes for Organic Light-Emitting Diodes with Radio Frequency Magnetron Sputter Deposition." *Appl. Phys. Lett.* 69:1611.
52. Suzuki, H. and S. Hoshino (1996). "Behavior of Charge Carriers and Excitons in Multilayer Organic Light-Emitting Diodes Made from a Polysilane Polymer as Monitored with Electroluminescence." *J. Appl. Phys.* 79: 858–865.
53. Tasch, S., W. Graupner, et al. (1995). "Red-Orange Electroluminescence with New Soluble and Air-Stable Poly(naphthalene-Vinylene)s." *Adv. Mat.* 7: 903.
54. Tasch, S., A. Niko, et al. (1996). "Highly Efficient Electroluminescence of New Wide Band Gap Ladder-Type Poly(Para-Phenylenes)." *Appl. Phys. Lett.* 68: 1090.
55. Tian, J., C. C. Wu, et al. (1995). "Photophysical Properties, Self-Assembled Thin Films, and Light-Emitting Íiodes of Poly(p-Pyridyl-vinylene)s and Poly(p-Pyridinium Vinylene)s." *Chem. Mat.* 7: 2190.
56. Yammoto, T., T. Inoue, et al. (1994). "Polymer Light-Emitting Diodes with Single- and Double-Layer Structures Using Poly(2,3-diphenylquinoxaline-5,8-diyl)." *Jpn. J. Appl. Phys.*: L250–L253.
57. Yang, Z., B. Hu, et al. (1995). "Polymer Electroluminescence Using ac or Reverse dc Biasing." *Macromolecules* 28: 6151.
58. Zyung, T., D. H. Hwang, et al. (1995). "Novel Blue Electroluminescent Polymers with Well-Defined Conjugation Length." *Chem. Mat.* 7: 1499.
59. Zyung, T., J. J. Kim, et al. (1995). "Electroluminescence from Poly(p-Phenylenevinylene) with Monoalkoxy Substituent on the Aromatic Ring." *Syn. Met.* 71: 2167–2169.

What is claimed:

1. An electroluminescent device, comprising:
   a. an anode;
   b. a cathode;
   c. an organic electroluminescent material including an organo-siloxane polymer, the main chain of said organo-siloxane polymer having an organic component comprising a polycyclic aromatic carbon network containing between 2 and 7 fused aromatic rings being substituted optionally with hydrogen, alkyl, aryl, heteroalkyl, heteroaralkyl, nitro, cyano, hydroxy, alkoxy, aryloxy, thio, alkylthio, arylthio, amino, halogen, dialkylamino, diarylamino, diaralkylamino, arylamino, alkylamino, arylalkylamino, carbonyloxy, carbonylalkoxy, carbonylalkyloxy, alkylcarbonyloxy, arylcarbonyloxy, alkoxylcarbonyloxy, sulfonyl, sulfonyloxy; provided that said organic component includes at least two covalent bonds coupling said organic component with said main chain; and
   d. said organic electroluminescent material being electroluminescently conductively coupled directly with said cathode and said anode such that said organic electroluminescent material emits light upon the application of a voltage across said cathode and said anode.

2. The electroluminescent device of claim 1, wherein said organic component is selected from the group consisting of electroluminescent agents, hole transport agents, electron transport agents, and combinations thereof.

3. The electroluminescent device of claim 2, wherein said organic component is an electroluminescent agent.

4. The electroluminescent device of claim 3, wherein said organic component is selected from the group consisting of anthracene and pentacene.

5. The electroluminescent device of claim 4, wherein said organic component comprises anthracene.

6. The electroluminescent device of claim 5, wherein said anthracene is coupled with a silicon atom in said main chain by at least one alkyl group.

7. The electroluminescent device of claim 6, wherein said alkyl group has the formula —$CH_2(CH_2)_mCH_2$—, where m is an integer between 1 and 4.

8. The electroluminescent device of claim 7, wherein anthracene is coupled with two silicon atoms in said main chain by two of said alkyl groups.

9. The electroluminescent device of claim 8, wherein m is 1 and said alkyl groups are placed at symmetric positions on said anthracene.

10. The electroluminescent device of claim 9, wherein said anthracene has the formula:

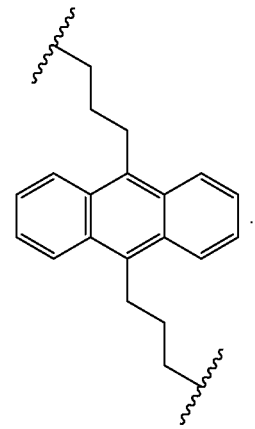

11. The electroluminescent device of claim 4, wherein said organic component comprises pentacene.

12. The electroluminescent device of claim 11, wherein said pentacene is coupled with a silicon atom in said main chain by at least one alkyl group.

13. The electroluminescent device of claim 12, wherein said alkyl group has the formula —$CH_2(CH_2)_mCH_2$—, where m is an integer between 1 and 4.

14. The electroluminescent device of claim 13, wherein said pentacene is coupled with two silicon atoms in said main chain by two of said alkyl groups.

15. The electroluminescent device of claim 14, wherein m is 1 and said alkyl groups are placed at symmetric positions on said pentacene.

16. The electroluminescent device of claim 15, wherein the pentacene has the formula:

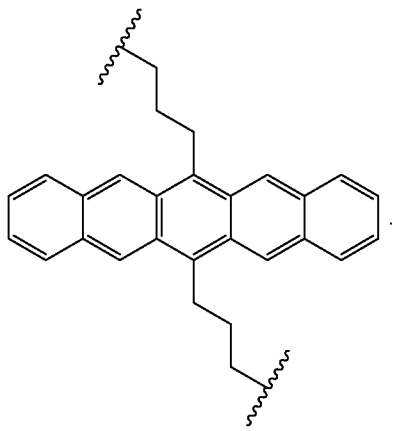

17. The electroluminescent device of claim 1, wherein said organic electroluminescent material further includes a dopant.

18. The electroluminescent device of claim 17, wherein said dopant is selected from the group consisting of hole transport materials, electron transport materials, and dyes.

19. The electroluminescent device of claim 18, wherein said dopant consists of a hole transport material.

20. The electroluminescent device of claim 19, wherein said hole transport material is a porphyrin or an aromatic tertiary amine.

21. The electroluminescent material of claim 18, wherein said dopant is a dye selected from the group consisting of coumarin, rhodamine perchlorate, and perylene.

22. The electroluminescent device of claim 4, further comprising a substrate coupled to one of said cathode and said anode.

23. The electroluminescent device of claim 1, wherein said organo-siloxane polymer is cross-linked by oxygen atoms to provide an organo-siloxane network.

24. An organic electroluminescent material, comprising
  a. an organic electroluminescent material including an organo-siloxane polymer, the main chain of said organo-siloxane polymer having an organic component comprising a polycyclic aromatic hydrocarbon containing between 2 and 7 fused aromatic rings being substituted optionally with hydrogen, alkyl, aryl, heteroalkyl, heteroaryl, nitro, cyano, hydroxy, alkoxy, aryloxy, thio, alkylthio, arylthio, amino, halogen, dialkylamino, diarylamino, diaralkylamino, arylamino, alkylamino, arylalkylamino, carbonyloxy, carbonylalkoxy, carbonylalkyloxy, alkylcarbonyloxy, arylcarbonyloxy, alkoxylcarbonyloxy, sulfonyl, sulfonyloxy; provided that said organic component includes at least two covalent bonds coupling said organic component with said main chain; and
  b. a second component selected from the group consisting of hole transporting materials, electron transport materials, dyes and combinations thereof; such that said electroluminescent material emits light upon the application of a voltage when said electroluminescent material is electroluminescently conductively coupled directly with a cathode and an anode.

25. The organic electroluminescent material of claim 24, wherein said organic component is selected from the group consisting of electroluminescent agents, hole transport agents, electron transport agents, and combinations thereof.

26. The organic electroluminescent material of claim 25, wherein said organic component is an electroluminescent agent.

27. The organic electroluminescent material of claim 26, wherein said organic component comprises anthracene.

28. The organic electroluminescent material of claim 27, wherein said anthracene is coupled with a silicon atom in said main chain by at least one alkyl group.

29. The organic electroluminescent material of claim 28, wherein said alkyl group has the formula —$CH_2(CH_2)_m CH_2$—, where m is an integer between 1 and 4.

30. The organic electroluminescent material of claim 29, wherein anthracene is coupled with two silicon atoms in said main chain by two of said alkyl groups.

31. The organic electroluminescent material of claim 30, wherein m is 1 and said alkyl groups are placed at symmetric positions on said anthracene.

32. The organic electroluminescent material of claim 31, wherein said anthracene has the formula:

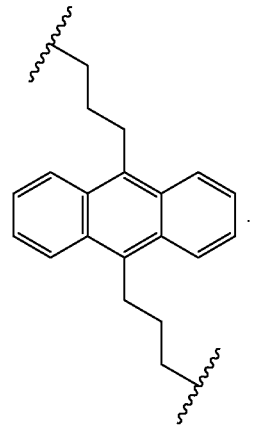

33. The organic electroluminescent material of claim 26, wherein said organic component comprises pentacene.

34. The organic electroluminescent material of claim 33, wherein said pentacene is coupled with a silicon atom in said main chain by at least one alkyl group.

35. The organic electroluminescent material of claim 34, wherein said alkyl group has the formula —$CH_2(CH_2)_m CH_2$—, where m is an integer between 1 and 4.

36. The organic electroluminescent material of claim 35, wherein said pentacene is coupled with two silicon atoms in said main chain by two of said alkyl groups.

37. The organic electroluminescent material of claim 36, wherein m is 1 and said alkyl groups are placed at symmetric positions on said pentacene.

38. The organic electroluminescent material of claim 37, wherein the pentacene has the formula:

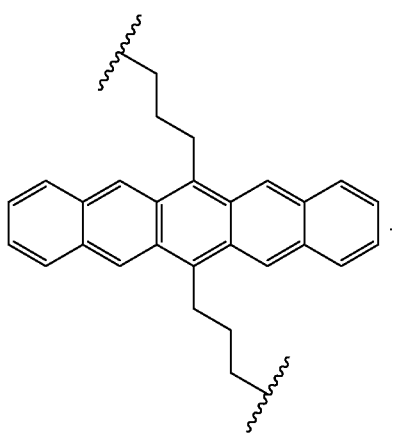

39. The organic electroluminescent material of claim 24, wherein said second component is a hole transport material.

40. The organic electroluminescent material of claim 39, wherein said hole transport material comprises a porphyrin or an aromatic tertiary amine.

41. The organic electroluminescent material of claim 24, wherein said second component is a dye selected from the group consisting of coumarin, rhodamine perchlorate, and perylene.

42. The organic electroluminescent material of claim 24, wherein said organo-siloxane polymer is cross-linked by oxygen atoms to provide an organo-siloxane network.

43. An organo-siloxane polymer, comprising a main chain including silicon, oxygen, and an organic component selected from the group consisting of anthracene and pentacene being substituted optionally with hydrogen, alkyl, aryl, heteroalkyl, heteroaryl, nitro, cyano, hydroxy, alkoxy, aryloxy, thio, alkylthio, arylthio, amino, halogen, dialkylamino, diarylamino, diaralkylamino, arylamino, alkylamino, aralkylamino, carbonyloxy, carbonylalkoxy, carbonylalkyloxy, alkylcarbonyloxy, arylcarbonyloxy, alkoxylcarbonyloxy, sulfonyl, sulfonyloxy, wherein said organic component is coupled with a silicon atom in said main chain by at least one alkyl group having the formula —CH$_2$(CH$_2$)$_m$CH$_2$—, wherein m is an integer between 1 and 4 provided that said organic component includes at least two covalent bonds coupling said organic component with said main chain, and wherein said polymer is electroluminescent.

44. The organo-siloxane polymer of claim 43, wherein anthracene is coupled with two silicon atoms in said main chain by two of said alkyl groups.

45. The organo-siloxane polymer of claim 44, wherein m is 1 and said alkyl groups are placed at symmetric positions on said anthracene.

46. The organo-siloxane polymer of claim 45, wherein said anthracene has the formula:

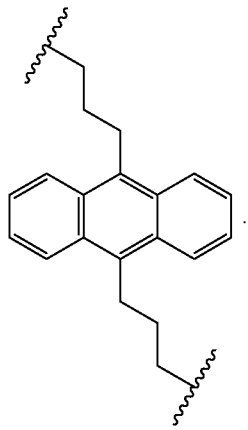

47. The organo-siloxane polymer of claim 43, wherein said pentacene is coupled with two silicon atoms in said main chain by two of said alkyl groups.

48. The organo-siloxane polymer of claim 47, wherein m is 1 and said alkyl groups are placed at symmetric positions on said pentacene.

49. The organo-siloxane polymer of claim 48, wherein said pentacene has the formula:

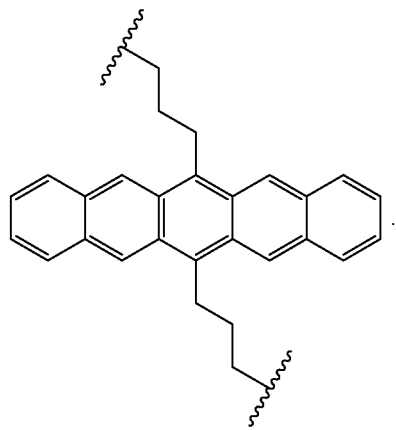

* * * * *